United States Patent
Xu

(10) Patent No.: US 8,323,656 B2
(45) Date of Patent: Dec. 4, 2012

(54) ANTIGEN DETERMINANT OF RHEUMATOID ARTHRITIS-SPECIFIC AUTOANTIBODY AND USE THEREOF

(76) Inventor: Yijun Xu, Mississauga (CA)

( * ) Notice: Subject to any disclaimer, the term of this patent is extended or adjusted under 35 U.S.C. 154(b) by 1045 days.

(21) Appl. No.: 11/767,775

(22) Filed: Jun. 25, 2007

(65) Prior Publication Data
US 2008/0318872 A1 Dec. 25, 2008

(51) Int. Cl.
| | |
|---|---|
| A61K 39/00 | (2006.01) |
| A61K 38/00 | (2006.01) |
| A61K 38/10 | (2006.01) |
| A61K 38/16 | (2006.01) |
| G01N 33/53 | (2006.01) |
| G01N 33/15 | (2006.01) |
| G01N 33/564 | (2006.01) |

(52) U.S. Cl. ..... 424/185.1; 530/326; 514/1.1; 514/21.4; 435/7.1; 435/7.92; 435/975; 436/509

(58) Field of Classification Search .................. None
See application file for complete search history.

(56) References Cited

U.S. PATENT DOCUMENTS

| | | | |
|---|---|---|---|
| 5,888,833 | A | 3/1999 | Serre et al. |
| 6,858,438 | B2 | 2/2005 | Van Venrooij et al. |
| 7,022,485 | B1 | 4/2006 | Serre et al. |
| 2006/0039924 | A1 | 2/2006 | Van Venrooij et al. |

FOREIGN PATENT DOCUMENTS

| | | |
|---|---|---|
| EP | 1541585 | 6/2005 |
| WO | WO9822503 | 5/1998 |
| WO | WO0146222 | 6/2001 |
| WO | WO2004078098 | 9/2004 |

OTHER PUBLICATIONS

I. Hoffman et al, "Diagnostic performance and predictive value of rheumatoid factor, anti-citrullinated peptide antibodies, and the HLA shared epitope for diagnosis of rheumatoid arthritis", Clin Chem, 50:261-263 (2004).
M. Hochberg et al, "The benefit/risk profile of TNF-blocking agents: findings of a consensus panel", Semin Arthritis Rheum, 34:819-836 (2005).
W. Hou et al, "Comparison of cathepsins K and S expression within the rheumatoid and osteoarthritic synovium", Arthritis Rheum, 46:663-674 (2002).
W. Hueber et al, "Antigen microarray profiling of autoantibodies in rheumatoid arthritis", Arthritis Rheum, 52:2645-2655 (2005).
W. Hueber et al, "Proteomic analysis of selected proteins in early rheumatoid arthritis: Anti-citrulline reactivity is associated with upregulation of proinflammatory cytokines", Ann Rheum Dis, ARD Online First, published on Aug. 10, 2006 as 10.1136/ard.2006. 054924.
T. Huizinga et al, "Refining the complex rheumatoid arthritis phenotype based on specificity of the HLA-DRB1 shared epitope for antibodies to citrullinated proteins", Arthritis Rheum, 52:3433-3438 (2005).

D. Huscher et al, "Cost of illness in rheumatoid arthritis, ankylosing spondylitis, psoriatic arthritis and SLE in Germany", Ann Rheum Dis, 65:1175-1183 (2006).
K. Ikari et al, "Association between PADI4 and rheumatoid arthritis. A replication study", Arthritis Rheum, 52:3054-3057 (2005).
Y. Ikeda et al, "Cathepsins B and L in synovial fluids from patients with rheumatoid arthritis and the effect of cathepsin B on the activation of pro-urokinase", J Med Invest, 47:61-75 (2000) (Abstract only).
N. Inanc et al, "Anti-CCP antibodies in rheumatoid arthritis and psoriatic arthritis", Clin Rheumatol, 26:17-23 (2007).
C. Indiveri et al, "The purified and reconstituted ornithine/citrulline carrier from rat liver mitochondria catalyses a second transport mode: ornithine+/H+ exchange", Biochem J, 341:705-711 (1999).
F. Ingegnoli et al, "Use of antibodies recognizing cyclic citrullinated peptide in the differential diagnosis of joint involvement in systeimic sclerosis", Clin Rheumatol, 26:510-514 (2007).
P. Irigoyen et al, "Regulation of anti-cyclic citrullinated peptide antibodies in rheumatoid arthritis: contrasting effects of HLA-DR3 and the shared epitope alleles", Arthritis Rheum, 52:3813-3818 (2005).
A. Ishigami et al, "Abnormal accumulation of citrullinated proteins catalyzed by peptidylarginine deiminase in hippocampal extracts from patients with Alzheimer's disease", J Neurosci Res, 80:120-128 (2005).
A. Jansen et al, "Rheumatoid factor and antibodies to cyclic citrullinated peptide differentiate rheumatoid arthritis from undifferentiated polyarthritis in patients with early arthritis", J Rheumatol, 29:2074-2076 (2002).

(Continued)

*Primary Examiner* — Phuong Huynh
(74) *Attorney, Agent, or Firm* — Ferris H. Lander, Inc.

(57) ABSTRACT

A dipeptide antigen determinant is disclosed where haptenic Cit and Cys residues are connected by means of a peptide bond having the formula III:

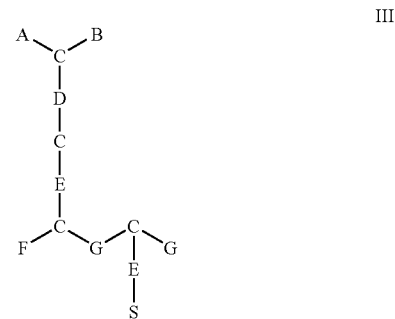

where A is —$NH_2$, B is —O—, D is —NH—, F is —NHCO—, or —NR—, where R is hydrogen or acyl, G is —CONH—, or —COOR, wherein R is alkyl, E is $(CH_2)_{n'}$, wherein n' is an integer from 1 to 6, S is —SH, or —SS—, on the condition that free thiol (SH) of Cys is crosslinked by a disulfide bond to another Cys. The antigen determinant reacts sensitively and specifically with serum autoantibodies present in patients suffering from rheumatoid arthritis (RA) which is useful for diagnosing or treating RA.

14 Claims, 6 Drawing Sheets

OTHER PUBLICATIONS

L. Jansen et al, "The predictive value of anti-cyclic citrullinated peptide antibodies in early arthritis", J Rheumatol, 30:1691-1695 (2003).

M. Johansson et al, "PTPN22 polymorphism and anti-cyclic citrullinated peptide antibodies in combination strongly predicts future onset of rheumatoid arthritis and has a specificity of 100% for the disease", Arthritis Res Ther, 8(1):R19 (2006).

S. Kaltenhauser et al, "Antibodies against cyclic citrullinated peptide are associated with the DRB1 shared epitope and predict joint erosion in rheumatoid arthritis", Rheumatology (Oxford), 46:100-104 (2007).

S. Kamali et al, "Anti-CCP and antikeratin antibodies in rheumatoid arthritis, primary Sjögren's syndrome, and Wegener's granulomatosis", Clin Rheumatol, 24:673-676 (2005).

C. Kang et al, "A functional haplotype of the PADI4 gene associated with increased rheumatoid arthritis susceptibility in Koreans", Arthritis Rheum, 54:90-96 (2006).

O. Kasapcopur et al, "Diagnostic accuracy of anti-cyclic citrullinated peptide antibodies in juvenile idiopathic arthritis", Ann Rheum Dis, 63:1687-1689 (2004).

A. Kastbom et al, "Anti-CCP antibody test predicts the disease course during 3 years in early rheumatoid arthritis (the Swedish TIRA project)", Ann Rheum Dis, 63:1085-1089 (2004).

A. Kavanaugh, "Economic issues with new rheumatologic therapeutics", Curr Opin Rheumatol, 19:272-276 (2007).

A. Kinloch et al, "Identification of citrullinated alpha-erolase as a candidate autoantigen in rheumatoid arthritis", Arthritis Res Ther, 7(6) R1421-R1429 (2005).

M. Koivula et al, "Inhibitory characteristics of citrullinated telopeptides of type I and II collagens for autoantibody binding in patients with rheumatoid arthritis", Rheumatology (Oxford), 45:1364-1369 (2006).

M. Koivula et al, "Are there autoantibodies reacting against citrullinated peptides derived from type I and type II collagens in patients with rheumatoid arthritis?", Ann Rheum Dis, 64:1443-1450 (2005).

M. Koivula et al, "Autoantibodies binding to citrullinated telopeptide of type II collagen and to cyclic citrullinated peptides predict synergistically the development of seropositive rheumatoid arthritis", Ann Rheum Dis, ARD Online First, published on May 1, 2007 as 10.1136/ard.2006.062919.

M. Koivula et al, "Sensitive immunoassay for the autoantibodies reacting against citrullinated carboxy-terminal telopeptides of type I and type II collagens in patients with rheumatoid arthritis", Clin Chem Lab Med, 43:1400-1405 (2005).

C. Korkmaz et al, "Anti-cyclic citrullinated peptide (CCP) antibodies in patients with long-standing rheumatoid arthritis and their relationship with extra-articular manifestations", Clin Biochem, 39:961-965 (2006).

E. Kroot et al, "The prognostic value of anti-cyclic citrullinated peptide antibody in patients with recent-onset rheumatoid arthritis", Arthritis Rheum, 43:1831-1835 (2000).

E. Kudo-Tanaka et al, "Autoantibodies to cyclic citrullinated peptide 2 (CCP2) are superior to other potential diagnostic biomarkers for predicting rheumatoid arthritis in early undifferentiated arthritis", Clin Rheumatol, (Feb. 8, 2007) (Abstract only).

K. Kuhn et al, "Antibodies against citrullinated proteins enhance tissue injury in experimental autoimmune arthritis", J Clin Invest, 116:961-973 (2006).

J. Kwok et al, "Anti-cyclic citrullinated peptide: diagnostic and prognostic values in juvenile idiopathic arthritis and rheumatoid arthritis in a Chinese population", Scand J Rheumatol, 34:359-366 (2005).

D. Lee et al, "Clinical utility of the anti-CCP assay in patients with rheumatic diseases", Ann Rheum Dis, 62:870-874 (2003).

Y. Lee et al, "PADI4 polymorphisms and rheumatoid arthritis susceptibility: a meta-analysis", Rheumatol Int, (Jan. 31, 2007) (Abstract only).

D. Ligeiro et al, "Influence of human leucocyte antigen-DRB1 on the susceptibility to rheumatoid arthritis and on the production of anti-cyclic citrullinated peptide antibodies in a Portuguese population", Ann Rheum Dis, 66:246-248 (2007).

L. Li et al, "Primary therapist model for patients referred for rheumatoid arthritis: a cost-effectiveness analysis", Arthritis Rheum, 55(3):402-410 (2006).

S. Limaye et al, "Antibodies to cyclic citrullinated peptide in patients with chronic arthritis attending an arthritis-monitoring monitoring clinic", J Clin Rheumatol, 11:150-152 (2005).

E. Lindqvist et al, "Mortality in rheumatoid arthritis patients with disease onset in the 1980s", Ann Rheum Dis, 58:11-14 (1999).

E. Lindqvist et al, "Prognostic laboratory markers of joint damage in rheumatoid arthritis", Ann Rheum Dis, 64:196-201 (2005).

S. Linn-Rasker et al, "Smoking is a risk factor for anti-CCP antibodies only in rheumatoid arthritis patients who carry HLA-DRB1 shared epitope alleles", Ann Rheum Dis, 65:366-371 (2006).

W. Li et al, "Inferring causal relarionships among intermediate phenotypes and biomarkers: a case study of rheumatoid arthritis", Bioinformatics, 22:1503-1507 (2006).

M. Lopez-Hoyos et al, "Clinical utility of anti-CCP antibodies in the differential diagnosis of elderly-onset rheumatoid arthritis and polymyalgia rheumatica", Rheumatology (Oxford), 43:655-657 (2004).

F. Lopez-Longo et al, "Anti-cyclic citrullinated peptide versus anti-Sa antibodies in diagnosis of rheumatoid arthritis in an outpatient clinic for connective tissue disease and spondyloarthritis", J Rheumatol, 33:1476-1481 (2006).

J. Low et al, "Determination of anti-cyclic citrullinated peptide antibodies in the sera of patients with juvenile idiopathic arthritis", J Rheumatol, 31:1829-1833 (2004).

M. Lu et al, "Native chemical ligation in covalent caspase inhibition by p35", Chem Biol, 13:117-122 (2005).

K. Lundberg et al, "Citrullinated proteins have increased immunogenicity and arthritogenicity and their presence in arthritic joints correlates with disease severity", Arthritis Res Ther, 7:R458-R467 (2005).

K. Machold et al, "Early rheumatoid arthritis", Curr Opin Rheumatol, 18:282-288 (2006).

E. Maier et al, "Induction of immune tolerance by oral IVIG", Int Immunopharmacol, 7:351-359 (2007).

A. Martinez et al, "PADI4 polymorphisma are not associated with rheumatoid arthritis in the Spanish population", Rheumatology (Oxford), 44:1263-1266 (2005).

A. Russell et al, "The role of anti-cyclic citrullinated peptide antibodies in predicting progression of palindromic rheumatism to rheumatoid arthritis", J Rheumatol, 33:1240-1242 (2006).

A. Russell et al, "Anti-cyclic citrullinated peptide antibodies in patients with rheumatoid arthritis treated with anti-tumour necrosis factor agents", Ann Rheum Dis, 64:1807 (2005).

K. Saegusa et al, "Cathepsin S inhibitor prevents autoantigen presentation and autoimmunity", J Clin Invest, 110:361-369 (2002).

N. Samanci et al, "Diagnostic value and clinical significance of anti-CCP in patients with advanced rheumatoid arthritis", J Natl Med Assoc, 97:1120-1126 (2005) (Abstract only).

A. Saraux et al, "Value of antibodies to citrulline-containing peptides for diagnosing early rheumatoid arthritis", J Rheumatol, 30:2535-2539 (2003).

U. Sauerland et al, "Clinical utility of the anti-CCP assay: experiences with 700 patients", Ann N Y Acad Sci, 1050:314-318 (2005).

G. Schellekens et al, "Citrulline is an essential constituent of antigenic determinants recognized by rheumatoid arthritis-specific autoantibodies", J Clin Invest, 101:273-281 (1998).

G. Schellekens et al, "The diagnostic properties of rheumatoid arthritis antibodies recognizing a cyclic citrullinated peptide", Arthritis Rheum, 43:155-163 (2000).

U. Schurigt et al, "Local expression of matrix metalloproteinases, cathepsins, and their inhibitors during the development of murine antigen-induced arthritis", Arthritis Res Ther, 7:R174-R188 (2005).

D. Scott et al, "Long-term outcome of treating rheumatoid arthritis: results after 20 years", Lancet, 1:1108-1111 (1987).

M. Sebbag et al, "Clinical and pathophysiological significance of the autoimmune response to citrullinated proteins in rheumatoid arthritis", Joint Bone Spine, 71:493-502 (2004).

M. Sebbag et al, "Epitopes of human fibrin recognized by the rheumatoid arthritis-specific autoantibodies to citrullinated proteins", Eur J Immuno, 36:2250-2263 (2006).

T. Senshu et al, "Preferential deimination of keratin K1 and filaggrin during the terminal differentiation of human epidermis", Biochem Biophys Res Commun, 225:712-719 (1996).

S. Shankar et al, "Role of anti cyclic citrullinated peptide antibodies in erosive disease in patients with rheumatoid arthritis", Indian J Med Res, 124:689-696 (2006).

G. Shi et al, "Cathepsin S required for normal MHC class II peptide loading and germiral center development", Immunity, 10:197-206 (1999).

O. Shovman et al, "The diagnostic utility of anti-cyclic citrullinated peptide antibodies, matrix metalloproteinase-3, rheumatoid factor, erythrocyte sedimentation rate, and C-reactive protein in patients with erosive and non-erosive rheumatoid arthritis", Clin Dev Immunol, 12:197-202 (2005).

S. Sihvonen et al, "The predictive value of rheumatoid factor isotypes, anti-cyclic citrullinated peptide antibodies, and antineutrophil cytoplasmic antibodies for mortality in patients with rheumatoid arthritis", J Rheumatol, 32:2089-2094 (2005).

S. Sihvonen et al, "Mortality in patients with rheumatoid arthritis treated with low-dose oral glucocorticoids. A population-based cohort study", J Rheumatol, 33:1740-1746 (2006).

G. Silverman, "Therapeutic B cell depletion and regeneration in rheumatoid arthritis: emerging patterns and paradigms", Arthritis Rheum, 54:2356-2367 (2006).

R. Singh et al, "Emerging biologic therapies in rheumatoid arthritis: cell targets and cytokines", Curr Opin Rheumatol, 17:274-279 (2005).

M. Skoumal et al, "Serum cathepsin K levels of patients with longstanding rheumatoid arthritis: correlation with radiological destruction", Arthritis Res Ther, 7:R65-R70 (2005).

K. Skriner et al, "Association of citrullinated proteins with synovial exosomes", Arthritis Rheum, 54:3809-3814 (2006).

J. Smolen et al, "Therapeutic strategies in early rheumatoid arthritis", Best Pract Res Clin Rheumatol, 19:163-177 (2005).

M. Soderlin et al, "Antibodies against cyclic citrullinated peptide (CCP) and levels of cartilage oligomeric matrix protein (COMP) in very early arthritis: relation to diagnosis and disease activity, Scand J Rheumatol, 33:185-188 (2004).

K. Solanki et al, "Anti-cyclic citrullinated antibodies: complementary to IgM rheumatoid factor in the early diagnosis of rheumatoid arthritis", N Z Med J, 117(1203):1-5 (2004).

A. Spadaro et al, "Methotrexate effect on anti-cyclic citrullinated peptide antibody levels in rheumatoid arthritis", Ann Rheum Dis, 64:1241-1242 (2005).

A. Spadaro et al, "Usefulness of anti-cyclic citrullinate peptide antibody determination in synovial fluid analysis of patients with rheumatoid arthritis", Reumatismo, 58:116-120 (2006).

A. Spadaro et al, "Anti-cyclic citrullinated peptide antibody determination in the synovial fluid of patients with rheumatoid arthritis: comment on the article by Caspi et al", Arthritis Rheum, 55:681-682 (2006).

W. Stohl et al, "B cell depletion therapy in systemic rheumatic diseases: different strokes for different folks?", Clin Immunol, 121:1-12 (2006).

A. Suzuki et al, "Functional haplotypes of PADI4, encoding citrullinating enzyme peptidylarginine deiminase 4, are associated with rheumatoid arthritis", Nat Genet, 34:395-402 (2003).

A. Suzuki et al, "Anti-citrullinated collagen type I antibody is a target of autoimmunity in rheumatoid arthritis", Biochem Biophys Res Commun, 333:418-426 (2005).

K. Suzuki et al, "High diagnostic performance of ELISA detection of antibodies to citrullinated antigens in rheumatoid arthritis", Scand J Rheumatol, 32:197-204 (2003).

M. Tamai et al, "The presence of anti-cyclic citrullinated peptide antibody is associated with magnetic resonance imaging detection of bone marrow oedema in early stage rheumatoid arthritis", Ann Rheum Dis, 65:133-134 (2006).

M. Tampoia et al, "Anti-cyclic citrullinated peptide autoantibodies measured by an automated enzyme immunoassay: analytical performance and clinical correlations", Clin Chim Acta, 355:137-144 (2005).

X. Tian et al, "Significance of citrullinated collagen type II and its antibodies in rheumatoid arthritis", Zhonghua Yi Xue Za Zhi, 86:2334-2338 (2006) (Abstract only).

G. Tobon et al, "Anti-cyclic citrullinated peptide antibodies in patients with primary Sjogren's syndrome", Ann Rheum Dis, 64:791-792 (2005).

A. Tonazzi et al, "Relationships of Cysteine and Lysine residues with the substrate binding site of the mitochondrial ornithine/citrulline carrier: an inhibition kinetic approach combined with the analysis of the homology structural model", Biochim Biophys Acta, 1718:53-60 (2005).

A. Tonazzi et al, "Chemical modification of the mitochondrial ornithine/citrulline carrier by SH reagents: effects on the transport activity and transition from carrier to pore-like function", Biochim Biophys Acta, 1611:123-130 (2003).

C. Turesson et al, "Rheumatoid factor and antibodies to cyclic citrullinated peptides are associated with severe extra-articular manifestations in rheumatoid arthritis", Ann Rheum Dis, 66:59-64 (2007).

J. Turkenburg et al, "Structure of a Cys25-->Ser mutant of human cathepsin S", Acta Crystallogr D Biol Crystallogr, 58:451-455 (2002).

A. Union et al, "Identification of citrullinated rheumatoid arthritis-specific epitope in natural filaggrin relevant for Antifilaggrin autoantibody detection by line immunoassay", Arthritis Rheum, 46:1185-1195 (2002).

I. Vallbracht et al, "Additional diagnostic and clinical value of anti-cyclic citrullinated peptide antibodies compared with rheumatoid factor isotypes in rtheumatoid arthritis", Autoimmun Rev, 4:389-394 (2005).

I. Vallbracht et al, „Diagnostic and clinical value of anti-cyclic citrullinated peptide antibodies compared with rheumatoid factor isotypes in rheumatoid arthritis, Ann Rheum Dis, 63:1079-1084 (2004).

B. Vander Cruyssen et al, "Diagnostic value of anti-human citrullinated fibrinogen ELISA and comparison with four other anti-citrullinated protein assays", Arthritis Res Ther, 8(4):R122 (2006).

B. Vander Cruyssen et al, "Prediction models for rheumatoid arthritis during diagnostic investigation: evaluation of combinations of rheumatoid factor, anti-citrullinated protein/peptide antibodies and the human leucocyte antigen-shared epitope", Ann Rheum Dis, 66:364-369 (2007).

A. Van Der Helm Van Mil et al, "The HLA-DRB1 shared epitope alleles are primarily a risk factor for anti-cyclic citrullinated peptide antibodies and are not an independent risk factor for development of rheumatoid arthritis", Arthritis Rheum, 54:1117-1121 (2006).

A. Van Der Helm Van Mil et al, "Antibodies to citrullinated proteins and differences in clinical progression of rheumatoid arthritis", Arthritis Res Ther, 7(5):R949-R958 (2005).

A. Van Der Helm Van Mil et al, "The HLA-DRB1 shared epitope alleles differ in the interaction with smoking and predisposition to antibodies to cyclic citrullinated peptide", Arthritis Rheum, 56:425-432 (2007).

F. Van Gaalen et al, "Autoantibodies to cyclic citrullinated peptides predict progression to rheumatoid arthritis in patients with undifferentiated arthritis: a prospective cohort study", Arthritis Rheum, 50:709-715 (2004).

F. Van Gallen et al, "Association between HLA class II genes and autoantibodies to cyclic citrullinated peptides (CCPs) influences the severity of rheumatoid arthritis", Arthritis Rheum, 50:2113-2121 (2004).

F. Van Gaalen et al, "A comparison of the diagnostic accuracy and prognostic value of the first and second anti-cyclic citrullinated peptides (CCP1 and CCP2) autoantibody tests for rheumatoid arthritis", Ann Rheum Dis, 64:1510-1512 (2005).

O. Vasiljeva et al, "Emerging roles of cysteine cathepsins in disease and their potential as drug targets", Curr Pharm Des, 13:385-401 (2007) (Abstract only).

J. Vencovsky et al, "Autoantibodies can be prognostic markers of an erosive disease in early rheumatoid arthritis", Ann Rheum Dis, 62:427-430 (2003).

K. Verpoort et al, "Association of HLA-DR3 with anti-cyclic citrullinated peptide antibody-negative rheumatoid arthritis", Arthritis Rheum, 52:3058-3062 (2005).

C. Vincent et al, "Anti-perinuclear factor compared with the so called "antikeratin" antibodies and antibodies to human epidermis filaggrin, in the diagnosis of arthritides", Ann Rheum Dis, 58:42-48 (1999).

C. Vincent et al, "Detection of antibodies to deiminated recombinant rat filaggrin by enzyme-linked immunosorbent assay: a highly effective test for the diagnosis of rheumatoid arthritis", Arthritis Rheum, 46:2051-2058 (2002).

O. Vittecoq et al, "Autoantibodies recognizing citrullinated rat filaggrin in an ELISA using citrullinated and non-citrullinated recombinant proteins as antigens are highly diagnostic for rheumatoid arthritis", Clin Exp Immunol, 135:173-180 (2004).

R. Voll et al, "Do we need new treatment that goes beyond tumor necrosis factor blockers for rheumatoid arthritis?", Ann N Y Acad Sci, 1051:799-810 (2005).

E. Vossenaar et al, "Citrullination of synovial proteins in murine models of rheumatoid arthritis", Arthritis Rheum, 48:2489-2500 (2003).

E. Vossenaar et al, "The presence of citrullinated proteins is not specific for rheumatoid synovial tissue", Arthritis Rheum, 50:3485-3494 (2004).

E. Vossenaar et al, "Absence of citrulline-specific autoantibodies in animal models of autoimmunity", Arthritis Rheum, 50:2370-2372 (2004).

E. Vossenaar et al, "Citrullination, a possible function link between susceptibility genes and rheumatoid arthritis", Arthritis Res Ther, 6:1-5 (2004).

B. Votta et al, "Peptide aldehyde inhibitors of cathepsin K inhibit bone resorption both in vitro and in vivo", J Bone Miner Res,12:1396-1406 (1997).

D. Wang et al, "Cathepsin K inhibitor-polymer conjugates: potential drugs for the treatment of osteoporosis and rheumatoid arthritis", Int J Pharm, 277:73-79 (2004).

L. Wang et al, "Expanding the genetic code", Angew Chem Int Ed Engl, 44:34-66 (2004).

S. Wang et al, "The structure of chagasin in complex with a cysteine protease clarifies the binding mode and evolution of an inhibitor family", Structure, 15:535-543 (2007).

Y. Wang et al, "Human PAD4 regulates histone arginine methylation levels via demethylimination", Science, 306:279-283 (2004).

Y. Ward et al, "Design and synthesis of dipeptide nitriles as reversible and potent Cathepsin S inhibitore", J Med Chem, 45:5471-5482 (2002).

E. Weidauer et al, "Effects of disease-modifying anti-rheumatic drugs (DMARDs) on the activities of rheumatoid arthritis-associated cathepsins K and S", Biol Chem, 388:331-336 (2007).

R. Yamada, Peptidylarginine deiminase type 4, anticitrullinated peptide antibodies, and rheumatoid arthritis, Autoimmun Rev, 4:201-206 (2005).

M. Yoshida et al, "Autoimmunity to citrullinated type II collagen in rheumatoid arthritis", Mod Rheumatol, 16:276-281 (2006).

Y. Yasuda et al, "The role of cathepsins in osteoporosis and arthritis: rationale for the design of new therapeutics", Adv Drug Deliv Rev, 57:973-993 (2005).

J. Zeng et al, "Evidence for inactivation of cysteine proteases by reactive carbonyls via glycation of active site thiols", Biochem J, 398:197-206 (2006).

X. Zeng et al, "Diagnostic value of anti-cyclic citrullinated peptide antibody in patients with rheumatoid arthritis", J Rheumatol, 30:1451-1455 (2003).

S. Zhou et al, "Immunological analysis of the amino terminal and the C8 isomer of human myelin basic protein", J Neuroimmunol, 46:91-96 (1993).

E. Clark et al, "How does B cell depletion therapy work, and how can it be improved?", Ann Rheum Dis, 64 Suppl 4: iv77-80 (2005).

D. Coenen et al, "Technical and diagnostic performance of 6 assays for the measurement of citrullinated protein/peptide antibodies in the diagnosis of rheumatoid arthritis", Clin Chem, 53:498-504 (2007).

B. Combe, "Early rheumatoid arthritis: strategies for prevention and management. Best practice & research", Best Pract Res Clin Rheumatol, 21:27-42 (2007).

P. Correa et al, "Anti-cyclic citrullinated peptide antibodies in rheumatoid arthritis: relation with clinical features, cytokines and HLA-DRB1", Biomedica, 24:140-152 (2004) (Abstract only).

C. Dejaco et al, "Diagnostic value of antibodies against a modified citrullinated vimentin in rheumatoid arthritis", Arthritis Res Ther, 8(4):R119 (2006).

N. Del Val Del Amo et al, "Anti-cyclic citrullinated peptide antibody in rheumatoid arthritis: relation with disease aggressiveness", Clin Exp Rheumatol, 24:281-286 (2006) (Abstract only).

L. Derycke et al, "Synovial intracellular citrullinated proteins colocalizing with peptidyl arginine deiminase as pathophysiologically relevant antigenic determinant of rheumatoid arthritis-specific humoral autoimmunity", Arthritis Rheum, 52:2323-2330 (2005).

L. Derycke et al, "Rheumatoid factor and anticitrullinated protein antibodies in rheumatoid arthritis: diagnostic value, associations with radiological progression rate, and extra-articular manifestations", Ann Rheum Dis, 63:1587-1593 (2004).

L. Derycke et al, "Rheumatoid factor, but not anti-citrullinated protein antibodies, is modulated by infliximab treatment in rheumatoid arthritis", Ann Rheum Dis, 64:299-302 (2005).

S. Desai et al, "An orally active reversible inhibitor of cathepsin S inhibits human trans vivo delayed-type hypersensitivity", Eur J Pharmacol, 538:168-174 (2006).

J. Deseze et al, "IgG reactivity against citrullinated myelin basic protein in multiple sclerosis", J Neuroimmunol, 117:149-155 (2001).

R. Devries et al, "Redefining the HLA and RA assoiation: to be or not to be anti-CP positive", J Autoimmun, 25Suppl):21-25 (2005).

R. Devries et al, "HLA and RA revisited: citrullinated food for the SE hypothesis, the DR6 effect, and NIMA", Hum Immunol, 67:454-459 (2006).

T. Doan et al, "Rheumatoid Arthritis: an overview of new and emerging therapies", J Clin Pharmacol, 45:751-762 (2005).

P. Dubrous et al, "Value of anti-cyclic citrullinated peptides antibodies in comparison with rheumatoid factor for rheumatoid arthritis diagnosis", Pathol Biol (Paris), 53:63-67 (2005).

S. Dubucquoi et al, "Evaluation of anti-citrullinated filaggrin antibodies as hallmarks for the diagnosis of rheumatic diseases", Ann Rheum Dis, 63:415-419 (2004).

R. Esser et al, "Cysteine proteinase inhibitors decrease articular cartilage and bone destruction in chronic inflammatory arthritis", Arthritis Rheum, 37:236-247 (1994).

D. Feng et al, "Citrullination preferentially proceeds in glomerular Bowman's capsule and increases in obstructive nephropathy", Kidney Int, 68:84-95 (2005).

Y. Feng et al, "Parallel detection of autoantibodies with microarrays in rheumatoid diseases", Clin Chem, 50:416-422 (2004).

A. Fernandez-Suarez et al, "Efficacy of three ELISA measurements of anti-cyclic citrullinated peptide antibodies in the early diagnosis of rheumatoid arthritis", Clin Chem Lab Med, 43:1234-1239 (2005).

A. Finckh et al, "B cell depletion may be more effective than switching to an alternative anti-tumor necrosis factor agent in rheumatoid arthritis patients with inadequate response to anti-tumor necrosis factor agents", Arthritis Rheum, 56:1417-1423 (2007).

K. Forslind et al, "Prediction of radiological outcome in early rheumatoid arthritis in clinical practice: role of antibodies to citrullinated peptides (anti-CCP)", Ann Rheum Dis, 63:1090-1095 (2004).

K. Forslind et al, "Sex: a major predictor of remission in early rheumatoid arthritis?", Ann Rheum Dis, 66:46-52 (2007).

K. Forslind et al, "Antifilaggrin autoantibodies in early rheumatoid arthritis", Scand J Rheumatol, 29:320-322 (2000).

K. Forslin et al, "Antifilaggrin autoantibodies in early rheumatoid arthritis may predict radiological progression", Scand J Rheumatol, 30:221-224 (2001).

I. Gao et al, "Determination of anti-CCP antibodies in patients with suspected rheumatoid arthritis: does it help to predict the diagnosis before referral to a rheumatologist?", Ann Rheum Dis, 64:1516-1517 (2005).

B. Garcia-Berrocal et al, "Anti-cyclic citrullinated peptide autoantibodies in IgM rheumatoid factor-positive patients", Clin Chim Acta, 354:123-130 (2005).

E. Girbal-Neuhauser et al, "The epitopes targeted by the rheumatoid arthritis-associated antifilaggrin autoantibodies are posttranslationally generated on various sites of (pro)filaggrin by deimination of arginine residues", J Immunol, 162:585-594 (1999).

F. Girelli et al, "Is anti cyclic citrullinated peptide a useful laboratory test for the diagnosis of rheumatoid arthritis?", Allerg Immunol (Paris), 36:127-130 (2004) (Abstract only).
D. Giustarini et al, "Altered thiol pattern in plasma of subjects affected by rheumatoid arthritis", Clin Exp Rheumatol, 23:205-212 (2005) (Abstract only).
Y. Goekoop-Ruiterman et al, "Comparison of treatment strategies in early rheumatoid arthritis: a randomized trial", Ann Intern Med, 146:406-415 (2007).
R. Goldbach-Mansky et al, "Rheumatoid arthritis associated autoantibodies in patients with synovitis of recent onset", Arthritis Res, 2:236-243 (2000).
N. Goodson et al, "Cardiovascular admissions and mortality in an inception cohort of patients with rheumatoid arthritis with onset in the 1980s and 1990s", Ann Rheum Dis, 64:1595-1601 (2005).
L. Gossee et al, "Prognostic factors for remission in early rheumatoid arthritis: a multiparameter prospective study", Ann Rheum Dis, 63:675-689 (2004).
P. Grabowski et al, "Elevated nitric oxide production in rheumatoid arthritis. Detection using the fasting urinary nitrate:creatinine ratio", Arthritis Rheum, 39:643-647 (1996).
A. Greiner et al, "Association of anti-cyclic citrullinated peptide antibodies, anti-citrullin antibodies, and IgM and IgA rheumatoid factors with serological parameters of disease activity in rheumatoid arthritis", Ann N Y Acad Sci, 1050:295-303 (2005).
S. Grootenboer-Mignot et al, "Second generation anti-cyclic citrullinated peptide (anti-CCP2) antibodies can replace other anti-filaggrin antibodies and improve rheumatoid arthritis diagnosis", Scand J Rheumatol, 33:218-220 (2004).
S. Gunatilleke et al, "Inhibition of lysosomal cysteine proteases by a series of Au(I) complexes: a detailed mechanistic investigation", J Med Chem, 49:3933-3937 (2006).
B. Gyorgy et al, "Citrullinations: a posttranslational modification in health and disease", Int J Biochem Cell Biol, 38:1662-1677 (2006).
T. Hagiwara et al, "Deimination of histone H2A and H4 at arginine 3 in HL-60 granulocytes", Biochemistry, 44:5827-5834 (2005).
T. Hagiwara et al, "Deimination of arginine residues in nucleophosmin/B23 and histones in HL-60 granulocytes", Biochem Biophys Res Commun, 290:979-983 (2002).
P. Hasler, "Biological therapies directed against cells in autoimmune disease", Springer Semin Immunopathol, 27:443-456 (2006).
G. Hayem et al, "Anti-Sa antibody is an accurate diagnostic and prognostic marker in adult rheumatoid arthritis", J Rheumatol, 26:7-13 (1999) (Abstract only).
H. Headlam et al, "Inhibition of cathepsins and related proteases by amino acid, peptide, and protein hydroperoxides", Free Radic Biol Med, 40:1539-1548 (2006).
A. Hida et al, "Nitric oxide acts on the mitochondria and protects human endothelial cells from apoptosis", J Lab Clin Med, 144:148-155 (2004).
S. Hida et al, "Influence of arginine deimination on antigenicity of fibrinogen", J Autoimmun, 23:141-150 (2004).
J. Hill et al, "Serum autoantibodies that bind citrullinated fibrinogen are frequently found in patients with rheumatoid arthritis", J Rheumatol, 33:2115-2119 (2006).
J. Hill et al, "The conversion of arginine to citrulline allows for a high-affinity peptide interaction with the rheumatoid arthritis-associated HLA-DRB1*0401 MHC class II molecule", J Immunol, 171:538-541 (2003).
C. Hitchon et al, "A distinct multicytokine profile is associated with anti-cyclical citrullinated peptide antibodies in patients with early untreated inflammatory arthritis", J Rheumatol, 31:2336-2346 (2004).
K. Hiura et al, "Examination of rheumatoid factor and other serum markers in rheumatoid arthritis", Yakugaku Zasshi, 125:881-887 (2005).
S. Abramson et al, "The role of nitric oxide in tissue destruction", Best Pract Res Clin Rheumatol, 15:831-845 (2001).
S. Agrawal et al, "Autoantibodies in rheumatoid arthritis association with severity of disease in established RA", Clin Rheumatol, 26:201-204 (2007).
K. Aho et al, "Epidemiology of rheumatoid arthritis in Finland", Semin Arthritis Rheum., 27:325-334 (1998).
G. Alenius et al, "Antibodies against cyclic citrullinated peptide (CCP) in psoriatic patients with or without joint inflammation", Ann Rheum Dis., 65:398-400 (2006).
C. Alessandri et al, "Decrease of anti-cyclic citrullinated peptide antibodies and rheumatoid factor following anti-TNFalpha therapy (infliximab) in rheumatoid arthritis is associated with clinical improvement", Ann Rheum Dis., 63:1218-1221 (2004).
D. Aletaha et al, "The rheumatoid arthritis in the clinic: comparing more than 1300 consecutive DMARD courses", Rheumatology (Oxford), 41:1367-1374 (2002).
C. Anzilotti et al, "Antibodies to viral citrullinated peptide in rheumatoid arthritis", J Rheumatol., 33:647-651 (2006).
S. Aotsuka et al, "A retrospective study of the fluctuation in serum levels of anti-cyclic citrullinated peptide antibody in patients with rheumatoid arthritis", Clin Exp Rheumatol., 23:475-481 (2005) (Abstract only).
A. Ates et al, "Predictive value of antibodies to cyclic citrullinated peptide in patients with early arthritis", Clin Rheumatol., 26:499-504 (2007).
F. Atzeni et al, "Adalimumab clinical efficacy is associated with rheumatoid factor and anti-cyclic citrullinated peptide antibody titer reduction: a one-year prospective study", Arthritis Res Ther., 8(1):R3 (2006).
I. Auger et al, "Influence of HLA-DR genes on the production rheumatoid arthritis-specific autoantibodies to citrullinated fibrinogen", Arthritis Rheum., 52:3424-3432 (2005).
J. Avouac et al, "Diagnostic and predictive value of anti-cyclic citrullinated protein antibodies in rheumatoid arthritis: a systematic literature review", Ann Rheum Dis., 65:845-851 (2006).
D. Baeten et al, "Specific presence of intracellular citrullinated proteins in rheumatoid arthritis synovium", Arthritis Rheum., 44:2255-2262 (2001).
A. Barton et al, "A functional haplotype of the PADI4 gene associated with rheumatoid arthritis in a Japanese is not associated in a United Kingdom population", Arthritis Rheum., 50:1117-1121 (2004).
A. Barton et al, "Investigation of polymorphisms in the PADI4 gene in determining severity of inflammatory polyarthritis", Ann Rheum Dis., 64:1311-1315 (2005).
S. Bas et al, "Anti-cyclic citrullinated peptide antibodies, IgM and IgA rheumatoid factors in the diagnosis and prognosis of rheumatoid arthritis", Rheumatology (Oxford), 42:677-680 (2003).
S. Bas et al, "Diagnostic tests for rheumatoid arthritis: comparison of anti-cyclic citrullinated peptide antibodies, anti-keratin antibodies and IgM rheumatoid factors", Rheumatology (Oxford), 41:809-814 (2002).
M. Benucci et al, "Correlation between different clinical activity and anti CC-P (anti-cyclic citrullinated peptide antibodies) titres in rheumatoid arthritis treated with three different tumor necrosis factors TNF-alpha blockers", Recenti Prog Med., 97:134-139 (2006) (Abstract only).
E. Berglin et al, "Radiological outcome in rheumatoid arthritis is predicted by presence of antibodies against cyclic citrullinated peptide before and at disease onset, and by IgA-RF at disease onset", Ann Rheum Dis., 65:453-458 (2006).
E. Berglin et al, "A combination of autoantibodies to cyclic citrullinated peptide (CCP) and HLA-DRB1 locus antigens is strongly associated with future onset of rheumatoid arthritis", Arthritis Res Ther., 6(4):R303-R308 (2004).
C. Bernardeau et al, "Nitric oxide in rheumatology", Joint Bone Spine, 68:457-462 (2001).
Biroc SL., Gay S., Hummel K., Magill C., Palmer JT., Spencer DR., Sa S., Klaus JL., Michel BA., Rasnick D., and Gay RE (2001). Cysteine protease activity is up-regulated in inflamed ankle joints of rats with adjuvant-induced arthritis and decreases with in vivo administration of a vinyl sulfone cysteine protease inhibitor.Arthritis Rheum. 44: 703-11.
N. Bizzaro et al, "Diagnostic accuracy of the anti-citrulline antibody assay for rheumatoid arthritis", Clin Chem., 47:1089-1093 (2001).
F. Bobbio-Pallavicini et al, "Autoantibody profile in rheumatoid arthritis during long-term infliximab treatment", Arthritis Res Ther, 6(3):R264-R272 (2004).

GT. Boire et al, "Anti-Sa antibodies and antibodies against cyclic citrullinated peptide are not equivalent as predictors of severe outcomes in patients with recent-onset polyarthritis", Arthritis Res Ther., 7(3):R592-R603 (2005).

M. Bombardieri et al, "Role of anti-cyclic citrullinated peptide antibodies in discriminating patients with rheumatoid arthritis from patients with chronic hepatitis C infection-associated polyarticular involvement", Arthritis Res Ther., 6(2): R137-R141 (2004).

T. Bongartz et al, "Citrullination in extra-articular manifestations of rheumatoid arthritis", Rheumatology (Oxford), 46:70-75 (2007).

S. Bongi et al, "Anti-cyclic citrullinated peptide antibodies are highly associated with severe bone lesions in rheumatoid arthritis anti-CCP and bone damage in RA", Autoimmunity, 37:495-501 (2004).

Y. Brauhn-Moscovici et al, "Anti-cyclic citrullinated protein antibodies as a predictor of response to anti-tumor necrosis factor-alpha therapy in patients with rheumatoid arthritis", J Rheumatol, 33:497-500 (2006).

D. Bromme et al, "Thiol-dependent cathepsins: pathophysiological implications and recent advances in inhibitor design", Curr Pharm Des, 8:1639-1658 (2002) (Abstract only).

J. Browning, "B cells move to centre stage: novel opportunities for autoimmune disease treatment", Nat Rev Drug Discov, 5:564-576 (2006).

L. Brulhart et al, "Efficacy of B cell depletion in patients with rheumatoid arthritis refractory to anti-tumour necrosis factor alpha agents: an open-label observational study", Ann Rheum Dis, 65:1255-1257 (2006).

H. Burkhardt et al, "Humoral immune response to citrullinated collagen type II determinants in early rheumatoid arthritis", Eur J Immunol, 35:1643-1652 (2005).

R. Callaghan et al, "Direct healthcare costs and predictors in patients with primary Sjogren's syndrome", Rheumatology (Oxford), 46:105-111 (2007).

T. Cantaert et al, "Citrullinated proteins in rheumatoid arthritis: crucial . . . but not sufficient!", Arthritis Rheum, 54:3381-3389 (2006).

L. Caponi et al, "A family based study show no association between rheumatoid arthritis and the PADI4 gene in a white French population", Ann Rheum Dis, 64:587-593 (2005).

P. Caramaschi et al, "Antibodies against cyclic citrullinated peptides in patients affected by rheumatoid arthritis before and after infliximab treatment", Rheumatol Int, 26:58-62 (2005).

D. Cash et al, "Synovial fluid levels of anti-cyclic citrullinated peptide antibodies and IgA rheumatoid factor in rheumatoid arthritis, psoriatic arthritis, and osteoarthritis", Arthritis Rheum, 55:53-56 (2006).

F. Ceccato et al, "The role of anticyclic citrullinated peptide antibodies in the differential diagnosis of elderly-onset rheumatoid arthritis and polymyalgia rheumatica", Clin Rheumatol, 25:854-857 (2006).

X. Chang et al, "The inhibition of antithrombin by peptidylarginine deiminase 4 may contribute to pathogenesis of rheumatoid arthritis", Rheumatology (Oxford), 44:293-298 (2005).

X. Chang et al, "Citrullination of fibronectin in rheumatoid arthritis synovial tissue", Rheumatology (Oxford), 44:1374-1382 (2005).

X. Chang et al, "Localization of peptidelarginine deiminase 4 (PADI4 and citrullinated protein in synovial tissue of rheumatoid arthritis", Rheumatology (Oxford), 44:40-50 (2005).

H. Chapman et al, "Emerging roles for cysteine proteases in human biology", Annu Rev Physiol, 59:63-88 (1997).

S. Chapuy-Regaud et al, "IgG subclass distribution of the rheumatoid arthritis-specific autoantibodies to citrullinated fibrin", Clin Exp Immunol, 139:542-550 (2005).

S. Chapuy-Regaud et al, "Fibrin deimination in synovial tissue is not specific for rheumatoid arthritis but commonly occurs during synovitides", J. Immunol, 174:5057-5064 (2005).

H. Chen et al, "The effect of etanercept on anti-cyclic citrullinated peptide antibodies and rheumatoid factor in patients with rheumatoid arthritis", Ann Rheum Dis, 65:35-39 (2006).

H. Chen et al, "Study of the proteins associated with Sa antigen", Zhonghua Yi Xue Za Zhi., 86:1896-1900 (2006) (Abstract only).

A. Chircorian et al, "Inhibition of lysosomal cysteine proteases by chrysotherapeutic compounds: a possible mechanism for the antiarthritic activity of Au(I)", Bioorg Med Chem Lett, 14:5113-5116 (2004).

K. Choi et al, "Clinical significance of anti-filaggrin antibody recognizing uncitrullinated filaggrin in rheumatoid arthritis", Exp Mol Med, 37:546-552 (2005).

S. Choi et al, "Diagnostic performances of anti-cyclic citrullinated peptides antibody and antifilaggrin antibody in Korean patients with rheumatoid arthritis", J Korean Med Sci, 20:473-478 (2005).

M. Mascelli et al, "Molecular, biologic, and pharmacokinetic properties of monoclonal antibodies: impact of these parameters on early clinical development", J Clin Pharmacol, 47:553-565 (2007).

C. Masson-Bessiere et al, "In the rheumatoid pannus, anti-filaggrin autoantibodies are produced by local plasma cells and constitute a higher proportion of IgG than in synovial fluid and serum", Clin Exp Immunol. 119: 544-552 (2000).

C. Masson-Bessiere et al, "The major synovial targets of the rheumatoid arthritis-specific antifilaggrin autoantibodies are deiminated forms of the $\alpha$- and $\beta$-chains of fibrin", J Immunol, 166:4177-4184 (2001).

T. Matsui et al, "Diagnostic utility of anti-cyclic citrullinated peptide antibodies for very early rheumatoid arthritis", J Rheumatol, 33:2390-2397 (2006).

K. Matsuo et al, "Identification of novel citrullinated autoantigens of synovium in rheumatoid arthritis using a proteomic approach", Arthritis Res Ther, 8(6):R175 (2006).

H. Menard et al, "Insights into rheumatoid arthritis derived from the Sa immune system", Arthritis Res, 2:429-432 (2000).

G. Merlini et al, "A deiminated viral peptide to detect antibodies in rheumatoid arthritis", Ann N Y Acad Sci, 1050:243-249 (2005).

D. Mewar et al, "Independent associations of anti-cyclic citrullinated peptide antibodies and rheumatoid factor with radiographic severity of rheumatoid arthritis", Arthritis Res Ther, 8(4):R128 (2006).

O. Meyer et al, "Anticitrullinated protein/peptide antibody assays in early rheumatoid arthritis for predicting five year radiographic damage", Ann Rheum Dis, 62:120-126 (2003).

O. Meyer et al, "Serial determination of cyclic citrullinated peptide autoantibodies predicted five-year radiological outcomes in a prospective cohort of patients with early rheumatoid arthritis", Arthritis Res Ther, 8(2):R40 (2006).

K. Michaud et al, "Direct medical costs and their predictors in patients with rheumatoid arthritis: a three-year study of 7577 patients", Arthritis Rheum, 48:2750-2762 (2003).

R. Mierau et al, "Diagnosis and prognosis of early rheumatoid arthritis, with special emphasis on laboratory analysis", Clin Chem Lab Med, 44:138-143 (2006).

T. Mikuls et al, "Anti-cyclic citrullinated peptide antibody and rheumatoid factor isotypes in African Americans with early rheumatoid arthritis", Arthritis Rheum, 54:3057-3059 (2006).

T. Mikuls et al, "Association of rheumatoid arthritis treatment response and disease duration with declines in serum levels of IgM rheumatoid factor and anti-cyclic citrullinated peptide antibody", Arthritis Rheum, 50:3776-3782 (2004).

T. Mimori, "Clinic significance of anti-CCP antibodies in rheumatoid arthritis", Intern Med, 44:1122-1126 (2005).

R. Mu et al, "Diagnostic significance of combined detection of rheumatoid factor and anticyclic citrullinated peptide antibodies in rheumatoid arthritis", Beijing Da Xue Xue Bao, 37:498-500 (2005) (Abstract only).

T. Nakagawa et al, "Impaired invariant chain degradation and antigen presentation and diminished collagen induced arthritis in cathepsin S null mice", Immunity, 10:207-217 (1999).

H. Nakamura et al, "Clinical significance of anti-citrullinated peptide antibody in Japanese patients with established rheumatoid arthritis", Scan J Rheumatol, 34:489-490 (2005).

V. Nell et al, "Autoantibody profiling as early diagnostic and prognostic tool for rheumatoid arthritis", Ann Rheum Dis, 64:1731-1736 (2005).

A. Nicholas et al, "Express of citrullinated proteins in murine experimental autoimmune encephalomyelitis", J Comp Neurol, 486:254-266 (2005).

A. Nicholas et al, "Increased citrullinated glial fibrillary acidic protein in secondary progressive multiple sclerosis", J Comp Neurol, 473:128-136 (2004).

M. Nielen et al, "Antibodies to citrullinated human fibrinogen (ACF) have diagnostic and prognostic value in early arthritis", Ann Rheum Dis, 64:1199-1204 (2005).

M. Nielen et al, "Stimultaneous development of acute phase response and autoantibodies in preclinical rheumatoid arthritis", Ann Rheum Dis, 65:535-537 (2006).

M. Nielen et al, "Specific autoantibodies precede the symptoms of rheumatoid arthritis: a study of serial measurements in blood donors", Arthritis Rheum, 50:380-386 (2004).

L. Nogueira et al, >> Performance of two ELISAs for antifilabbrin autoantibodies, using either affinity purified or deiminated recombinant human filaggrin, in the diagnosis of rheumatoid arthritis, Ann Rheum Dis, 60:882-887 (2001).

K. Nomura, "Specificity and mode of action of the muscle-type protein-arginine deiminase", Arch Biochem Biophys, 293:362-369 (1992).

M. Nurmohamed et al, "Efficacy, tolerability and cost effectiveness of disease-modifying antirheumatic drugs and biologic agents in rheumatoid arthritis", Drugs, 65:661-694 (2005).

Y. Okazaki et al, "Identification of citrullinated eukaryotic translation initiation factor 4G1 as novel autoantigen in rheumatoid arthritis", Biochem Biophys Res Commun, 341:94-100 (2006).

J. Oliver et al, "Genetic epidemiology of rheumatoid arthritis", Curr Opin Rheumatol, 18:141-146 (2006).

D. Ollendorf et al, "Impact of leflunomide versus biologic agents on the costs of care for rheumatoid arthritis in a managed care population", Am J Manag Care, 8:S203-S213 (2002).

T. Palosuo et al, "Purification of filaggrin from human epidermis and measurement of antifilaggrin autoantibodies in sera from patients with rheumatoid arthritis by an enzyme-linked immunosorbent assay", Int Arch Allergy Immunol, 115:294-302 (1998).

R. Panchagnula et al, "Role of anticyclic citrullinated peptide in the diagnosis of early rheumatoid factor-negative suspected rheumatoid arthritis: is it worthwhile to order the test?", J Clin Rheumatol, 12:172-175 (2006).

M. Pedersen et al, "Environmental risk factors differ between rheumatoid arthritis with and without auto-antibodies against cyclic citrullinated peptides", Arthritis Res Ther, 8(4):R133 (2006).

M. Pierer et al, "Association of PTPN22 1858 single-nucleotide polymorphism with rheumatoid arthritis in a German cohort: higher frequency of the risk allele in male compared to female patients", Arthritis Res Ther, 8(3):R75 (2006).

G. Pinheiro et al, "Anti-cyclic citrullinated peptide antibodies in advanced rheumatoid arthritis", Ann Intern Med, 139:234-235 (2003).

C. Popa et al, "Repeated B lymphocyte depletion with rituximab in rheumatoid arthritis over 7 yrs", Rheumatology (Oxford), 46:626-630 (2007).

F. Pratesi et al, "Deiminated Epstein-barr virus nuclear antigen 1 is a target of anti-citrullinated protein antibodies in rheumatoid arthritis", Arthritis Rheum, 54:733-741 (2006).

F. Puppo et al, "Emerging biologic drugs for the treatment of rheumatoid arthritis", Autoimm Rev, 4:537-541 (2005).

M. Quinn et al, "Anti-CCP antibodies measured at disease onset help identify seronegative rheumatoid arthritis and predict radiological and functional outcome", Rheumatology (Oxford), 45:478-480 (2005).

R. Raijmakers et al, "Citrullnation of central nervous system proteins during the development of experimental autoimmune encephalomyelitis", J Comp Neurol, 486:243-253 (2005).

S. Rantapaa-Dahlqvist, "Diagnostic and prognostic significance of autoantibodies in early rheumatoid arthritis", Scand J Rheumatol, 34:83-96 (2005).

S. Rantapaa-Dahlqvist et al, "Up regulation of monocyte chemoattractant protein-1 expression in anti-citrulline antibody and immunoglobulin M rheumatoid factor positive subjects precedes onset of inflammatory response and development of overt rheumatoid arthritis", Ann Rheum Dis, 66:121-123 (2007).

K. Raza et al, "Predictive value of antibodies to cyclic citrullinated peptide in patients with very early inflammatory arthritis", J Rheumatol, 32:231-238 (2005).

E. Redaitene et al, "Prognostic value of some serological markers of rheumatoid arthritis in assessment of x-ray outcome of the disease", Ter Arkh, 78:67-70 (2006) (Abstract only).

B. Relic et al, "TNF-alpha protects human primary articular chondrocytes from nitric oxide-induced apoptosis via nuclear factor-kappaB", Lab Invest, 82:1661-1672 (2003).

C. Reparon-Schuijt et al, "Secretion of anti-citrulline-containing peptide antibody by B lymphocytes in rheumatoid arthritis", Arthritis Rheum, 44:41-47 (2001).

M. Rodriguez-Mahon et al, "Association of anti-cyclic citrullinated peptide and anti-Sa/citrullinated vimentin autoantibodies in rheumatoid arthritis", Arthritis Rheum, 55:657-661 (2006).

J. Ronnelid et al, "Longitudinal analysis of citrullinated protein/peptide antibodies (anti-CP) during 5 year follow up in early rheumatoid arthritis: anti-CP status predicts worse disease activity and greater radiological progression", Ann Rheum Dis, 64:1744-1749 (2005).

E. Rosloniec et al, "Second-generation peptidomimetic inhibitors of antigen presentation effectively treat autoimmune diseases in HLA-DR-transgenic mouse models", J Autoimmun, 27:182-195 (2006).

B. Rubin et al, "Citrullination of self-proteins and autoimmunity", Scand J Immunol, 60:112-120 (2004).

E. Vossenaar et al, "Rheumatoid arthritis specific anti-Sa antibodies target citrullinated vimentin", Arthritis Research & Therapy, 6(2):R142-R150 (Feb. 2004).

Formula Sheet

```
                              SEQUENCE LISTING

<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic Polyepitope peptide
<220> FEATURE:
<221> NAME/KEY: misc_feature
<222> LOCATION: (1)..(21)
<223> OTHER INFORMATION: Xaa is citrulline

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Polyepitope peptide
<220> FEATURE:
<221> NAME/KEY: misc_feature
<222> LOCATION: (1)..(1)
<223> OTHER INFORMATION: Xaa is citrulline
<220> FEATURE:
<221> NAME/KEY: misc_feature
<222> LOCATION: (3)..(9)
<223> OTHER INFORMATION: Xaa is citrulline
<220> FEATURE:
<221> NAME/KEY: misc_feature
```

```
<222> LOCATION: (12)..(15)
<223> OTHER INFORMATION: Xaa is citrulline
<220> FEATURE:
<221> NAME/KEY: misc_feature
<222> LOCATION: (17)..(18)
<223> OTHER INFORMATION: Xaa is citrulline
<220> FEATURE:
<221> NAME/KEY: misc_feature
<222> LOCATION: (20)..(20)
<223> OTHER INFORMATION: Xaa is citrulline

<400> SEQUENCE: 2

Xaa Cys Xaa Xaa Xaa Xaa Xaa Xaa Xaa Cys Cys Xaa Xaa Xaa Xaa Cys
1               5                   10                  15

Xaa Xaa Cys Xaa Cys
            20
```

ANTIGEN DETERMINANT OF RHEUMATOID ARTHRITIS-SPECIFIC AUTOANTIBODY AND USE THEREOF

FIELD OF THE INVENTION

The present invention relates to compositions and sequences of an antigen determinant derived from an autoantigen recognized by autoantibodies from patients with rheumatoid arthritis (RA) and to their applications in diagnosis, prevention and treatment of the disease.

BACKGROUND OF THE INVENTION

RA is a chronic inflammatory autoimmune disease of unknown etiology. Although several therapeutic modalities exist for the treatment of RA, at present there is no cure. RA affects about 1% of the population worldwide, and 2% of the adults aged 65 and older. RA can start at any age and its prevalence is nearly three times more common in women than men. RA is a disease which shows poor long-term prognosis. Statistics indicate that 80 percent of affected patients are disabled after 20 years, and life expectancy is reduced by an average of 3 to 18 years.

RA is a major cause of disability, morbidity and mortality. RA is characterized by symmetric inflammation of synovial joints that leads to progressive erosions of cartilage and bone. This process attacks the cartilage by following a so-called pannus and erodes the underlying bone by recruiting osteoclasts. Tendons and other body parts are further affected. Since damaged joints are normally irreparable, this often led to permanent incapacitation. For most untreated RA patients, irreversible joint damage occurs within 2 years.

In terms of personal, social and economic costs, the effects of RA are substantial. Recent studies indicate that the mean annual medical cost for each patient was $6300 USD in the United States, $6800 CND in Canada, € 4700 in Germany and £2700 in the United Kingdom. The total annual costs for RA care are currently about $2 billion in Canada and $18 billion in the United States; a number that is expected to increase dramatically with an aging population.

Novel ideas for the development of drugs that specifically treat RA with minimal adverse events and costs are urgently needed. The classical paradigm for RA pathogenesis holds that CD4+ T cells mediate joint damage both directly and by driving non-T effector cells to release inflammatory cytokines. Disease modifying antirheumatic drugs (DMARDs) are the mainstay of treatment of RA, however they suffer from limited efficacy, toxicity problems or both. Biological based interventional therapies, such as TNFα antagonists have shown marked anti-inflammatory affects, however there are severe risks associated with their use. Only about 60-70% of RA patients so treated show an ACR20 response (defined as the minimal acceptable response to be achieved for a RA patient to have responded to a drug). The costs of biologicals are about 2 to 7 times that of the DMARDs, however none of these therapies are effective at blocking disease progression.

Gold drugs, as the "gold standard" of therapy, have been used to treat RA for over 78 years to retard and sometimes cause remissions of the disease. The mechanism of gold for antiarthritic activity was based on the active site directed inactivation of the T cell and cysteine (Cys) proteases, particularly cathepsins, by formation of chelate complexes between gold and Cys thiol groups of the affected antigenic peptide and cathepsins. Highly expressed cathepsins as direct contributors to inflammation and cartilage and bone degradation were detected both in synovial membrane and fluid in RA. The activities of cathepsins were significantly correlated with the concentration of inflammatory cytokines such as interleukin-1β (IL-1β) and TNFα. Early clinical data with cathepsin inhibitors showed potential that it may be effective for RA care. The selective inhibition of cathepsins by modification of the thiol moiety may potentially lead to the development of a novel chemotherapeutic treatment for RA. The progress in cathepsin inhibitors design and synthesis has been advanced by the substantial interest of pharmaceutical companies such as Apotex, AstraZeneca, Aventis, Bayer, Bochringes Ingelheim, Celera Genomics, GlaxoSmithKline, Merck, and Novartis.

The new paradigm for RA pathogenesis focuses on an interaction between B cells and CD4+ T cells. Anti-CD20 rituximab based B-lymphocyte depletion (BLyD) therapy has therapeutic potential for patients with RA. BLyD led B cells disappear within days but clinical improvement and autoantibody decline may progress over as long as 9 months. Sustained clinical responses with an impressive improvement was seen for up to 1 year according to ACR50-70 criteria (defined as the good and excellent response to be achieved for a RA patient to have responded to a drug), reported in case reports, open-label pilot studies, and a randomized, double-blind, placebo-controlled trial. BLyD used in combination with DMARDs methotrexate or cyclophosphamide appears to be a reasonable treatment option for refractory RA. These positive responses were associated with a major decline in C Reactive Protein (CRP) and autoantibody levels including all classes of rheumatoid factor (RF) and second anti-cyclic citrullinated peptides (anti-CCP 2). Memory B cells from RA patients were more sensitive to Rituximab than memory cells from normal controls. Defective B cell tolerance checkpoints were seen from patients with RA that may favor the development of autoimmunity. It is likely that the clinical pathology of RA is antibody-mediated and BLyD prevents replenishment from B cells. Qualitative or quantitative differences in B cell commitment in RA pathobiology might have a function in the different responses observed. The effects of BLyD lend increasing support to the idea that both inflammatory effector mechanism and underlying immunoregulatory disturbance in RA are driven by autoantibody rather than by T cells. This realization represents a significant leap forward in understanding the pathogenic mechanism of RA. The generation of rare pathogenic B cell subsets may be a rate-limiting step in the pathogenesis of RA.

Although BLyD shows great promise and reveals mechanism of the disease, there is not yet a long-term strategy for routine use. Chronically maintained depletion with frequently repeated BlyD is unlikely to be a viable option, even in a case with sustained benefit, since such treatment may induce hypogammaglobulinaemia and serious infections. Identifying the relevant antigen that drives the pathogenic mechanism in RA is crucial to form an antigen-based immunointervention, e.g., tolerizing vaccine. It would be preferable to induce the death of autoimmune B cells by antigens with the absolute certainty that said antigens administration will never induce or recall a pathogenic response. Small molecules that specifically discourage the survival of autoreactive B cells in the disease should provide an efficient and cost-effective treatment of RA. Gold thiomalate as the blockade of thiols is a perfect drug for RA because it can induce complete and permanent remission but the problem is that it achieves this very rarely, and more often produces toxicity. There is no reason to not think that if we understand how drugs like gold really work it should not be possible to separate efficacy from toxicity. It is reasonable to hope that further development of strategies targeting pathogenic B-cell clones will extend this toward the original aim of truly long-term remission of RA.

A "window of therapeutic opportunity" has been suggested to be present within the first 3 months of the onset of the disease symptom. Timely intervention is crucial in preventing irreversible joint damage and diagnosis and aggressive therapy during the earliest stages of RA could significantly improve its medical and economic outcome.

The 1987 RA classification criteria of the American College of Rheumatology (ACR) were developed using patients with established RA (mean disease duration close to 8 years) having 91% sensitivity and 89% specificity. RA is routinely defined in clinical practice by the presence of least 4 of the 7 criteria, wherein clinical criteria 1 through 4 must be present for over 6 weeks. These ACR criteria are often not manifested in early RA. RF is the only serological marker included in the ACR criteria. RF can be detected in 50-80% of RA sera, but is frequently present in healthy individuals (especially elderly), and in patients with infections and other autoimmune diseases. Diagnosis of RA using RF testing remains suboptimal. The ACR criteria have served rheumatologists well for decades for established RA but they remain inadequate due to limited usefulness in early RA.

New criteria are urgently needed to shift from classifying established RA to classifying early RA that is projected to become persistent and erosive disease. The new criteria should include reliable serological marker that detects RA in early stages both highly specifically and sensitively. The new measure will lead to a definitive diagnosis of early RA with enhanced ability to prognosis the disease outcome.

The recent discovery of citrullinated protein/peptide (CP) bound autoantibodies as highly specific diagnostic markers for RA has revolutionized the early serodiagnostic evaluation of patients with RA and represents the first commercially available assay that approaches this goal. Posttranslational modification of self-protein with citrullination involvement has been suggested to be a crucial step in the generation of neoepitopes responding to production of RA-specific antibodies. Endogenous peptidylarginine deiminase (PAD) enzymes catalyze the conversion of peptidyl arginine to peptidyl citrulline. Non-coded amino acid citrulline (Cit) has been suggested as the neoepitope of acquired antigenicity of protein through deimination.

Along with the immunological findings on citrullination in proteins, a genetic connection between PADI4 and RA has been reported to be associated in the Japanese and Korean populations. But, the association was not replicated in the Caucasians, Spanish and UK populations. A family based study also showed no association between PADI4 and RA in a white French population. No evidence was found for the association of the PADI4 gene with severity as assessed by erosive outcome or with presence of antibodies against citrullinated antigen in patients with inflammatory polyarthritis.

Antibodies to CP are locally produced in the inflamed synovium, PADI2 and PADI4 are also localized in synovial tissue. These findings suggest a possibility that local citrullination of intra- and extra-articular proteins might be the initial event leading to autoantibody production in RA. CP derived from α-erolase, fibrin, fibrinogen, fibronectin, and vimentin in synovial tissue or joints, keratin, perinuclear factor, and filaggrins in epithelial tissues, type I and II collagen (CI, CII) in cartilage-specific extracellular matrix, and viral peptide in EBV infected B lymphocytes and epithelial cells of the oropharynx, have been suggested as the autoantigen candidates. Besides these, citrullinated asporin, cathepsin D, β-actin, CapZα-1, albumin, eukaryotic translation initiation factor 4, histamine receptor, protein disulfide-isomerase (PDI) ER60 precursor, mitochondrial aldehyde dehydrogenase (ALDH2), and Sp alpha (CD5 antigen-like protein) receptor were identified as the candidate citrullinated autoantigens in RA. Proteomic approach identified 51 (5.2%) of the visualized 990 synovial proteins from patients with RA were citrullinated. Ninety-four (9.5%) of the 990 protein spots were reactive to the RA sera. Interestingly, 30 (31.9%) of the 94 RA sera-reactive spots were CP and 30 (58.8%) of the 51 CP were RA sera-reactive. But, researchers have thus far failed to demonstrate that CP act as driving antigens for the induction of arthritogenicity and autoimmunity in experimental mouse arthritis models. Increased immunogenicity and arthritogenicity were seen when mice were immunized with CP in the presence of adjuvant, and none of the mice investigated developed arthritis. In collagen-induced arthritis however, linear citrullinated peptide (LCP) tolerized mice demonstrated significantly reduced disease severity and incidence compared with controls. Citrullinated fibrin was observed from any synovitis in synovial tissue from RA patients and control patients. There were citrullination of histones and nucleophosmin/B23 in HL-60 granulocytes, and citrullination of keratins and antithrombin in epidermis and plasma. Citrullination was detected in lung specimens of patients with RA-associated IP and patients with IP and control patients. Abnormally accumulated CP was detected in hippocampal extracts from patients with Alzheimers disease. Citrullination of myelin basic protein was observed during development of experimental autoimmune encephalomyelitis. Brain proteins with citrullination were correlated to the pathophysiology of multiple sclerosis brains. CP was also found in Browmans capsules and in obstructive nephropathy. Thus, citrullination is a general phenomenon of posttranslational modification of self-protein. Citrullination is crucial but not essential in induce an autoimmune response with production of RA-specific antibodies. Citrulination is incapable of induce an autoimmune response with production of antibodies unrelated to RA. The profile of citrullination in immunogenicity of the autoantigen has been poorly understood. The origin of Cit-containing autoantigen involved in the induction of RA-specific antibodies remains elucidative.

RA-specific antibodies have been classified into anti-CP (antibody against CP derived from α-enolase, CI, CII, fibrin, filaggrin, keratin, perinuclear factor, or vimentin), anti-LCP (antibody against LCP derived from profilaggrin, filaggrin, CI, CII, or EBV nuclear antigen), anti-CCP1 (antibody against single CCP derived from filaggrin) and anti-CCP2 (antibody against artificial CCPs derived from peptide libraries with non homologous from known proteins) based on capture antigen used to detect them. Anti-CP test showed high specificity (~100%) at low sensitivity (46%) (n=8941) (Palosuo et al., 1998; Hayem et al., 1999; Vincent et al., 1999; Forslin et al., 2000; Goldbach-Mansky et al., 2000; Menard et al., 2000; Nogueira et al., 2001; Bas et al., 2002; Vincent et al., 2002; Meyer et al., 2003; Saraux et al., 2003; Suzuki et al., 2003; Suzuki et al., 2003; Vencovsky et al., 2003; Dubucquoi et al., 2004; Grootenboer-Mignot et al., 2004; Vittecoq et al., 2004; Auger et al., 2005; Boire et al., 2005; Greiner et al., 2005; Kinloch et al., 2005; Nielen et al., 2005; Suzuki et al., 2005; Chen et al., 2006; Dejaco et al., 2006; Hill et al., 2006; Lopez-Longo et al., 2006; Matsuo et al., 2006; Rodriguez-Mahou et al., 2006; Tian et al., 2006; Vander Cruyssen et al., 2006; Yoshida et al., 2006; Agrawal et al., 2007; Coenen et al., 2007). A similar specificity (~100%) and sensitivity (48%) were detected when either naturally derived or chemically synthesized LCP were used as capture antigen (n=3668) (Schellekens et al., 1998; Girbal-Neuhauser et al., 1999;

Schellekens et al., 2000; Union et al., 2002; De Rycke et al., 2004; Dubucquoi et al., 2004; Hoffman et al., 2004; Low et al., 2004; Burhardt et al., 2005; Koivula et al., 2005; Merlini et al., 2005; Anzilotti et al., 2006; Koivula et al., 2006; Pratesi et al., 2006; Vander Cruyssen et al., 2006; Vander Cruyssen et al., 2007). Using CCP considerably increased sensitivity in comparison with its LCP counterpart without sacrificing specificity, anti-CCP1 were 53% sensitivity at ~100% specificity (n=2948) (Goldbach-Mansky et al., 2000; Kroot et al., 2000; Schellekens et al., 2000; Bizzaro et al., 2001; Bas et al., 2002; Jansen et al., 2002; Vincent et al., 2002; Bas et al., 2003; Jansen et al., 2003; Meyer et al., 2003; Saroux et al., 2003; Vencovsky et al., 2003; Zeng et al., 2003; Feng et al., 2004; van Gaalen et al., 2005; Vander Cruyssen et al., 2006), and anti-CCP2 were 66% sensitivity at ~100% specificity (n=19385) (Lee et al., 2003; Pinheiro et al., 2003; Suzuki et al., 2003; Alessandri et al., 2004; Berglin et al., 2004; Bobbio-Pallavicini et al., 2004; Bombardien et al., 2004; Bongi et al., 2004; Correa et al., 2004; De Rycke et al., 2004; Dubucquoi et al., 2004; Forslind et al., 2004; Girelli et al., 2004; Grootenboer-Mignot et al., 2004; Hitchon et al., 2004; Kasapcopur et al., 2004; Kastbom et al., 2004; Lopez-Hoyos et al., 2004; Low et al., 2004; Mikuls et al., 2004; Soderlin et al., 2004; Solanki et al., 2004; Vallbracht et al., 2004; van Gaalen et al., 2004; Vittecoq et al., 2004; Aotsuka et al., 2005; Boire et al., 2005; Burkhardt et al., 2005; Caramaschi et al., 2005; Choi et al., 2005; Dubrous et al., 2005; Femandez-Suarez et al., 2005; Gao et al., 2005; Garcia-Berrocal et al., 2005; Greiner et al., 2005; Hiura et al., 2005; Huizinga et al., 2005; Irigoyen et al., 2005; Kamali et al., 2005; Koivula et al., 2005; Kwok et al., 2005; Limaye et al., 2005; Lindqvist et al., 2005; Mu et al., 2005; Nakamura et al., 2005; Nell et al., 2005; Nielen et al., 2005; Quinn et al., 2005; Raza et al., 2005; Ronnelid et al., 2005; Samanci et al., 2005; Sauerland et al., 2005; Shovman et al., 2005; Sihvonen et al., 2005; Spadaro et al., 2005; Tampoia et al., 2005; Tobon et al., 2005; van der Helm-van Mil et al., 2005; van Gaalen et al., 2005; Verpoort et al., 2005; Alenius et al., 2006; Ates et al., 2006; Atzeni et al., 2006; Benucci et al., 2006; Berglin et al., 2006; Braun-Moscovici et al., 2006; Caspi et al., 2006; Ceccato et al., 2006; Chen et al., 2006; Dejaco et al., 2006; del Val del Amo et al., 2006; Hill et al., 2006; Inanc et al., 2006; Johansson et al., 2006; Koivula et al., 2006; Korkmaz et al., 2006; Linn-Rasker et al., 2006; Lopez-Longo et al., 2006; Matsui et al., 2006; Mewar et al., 2006; Meyer et al., 2006; Mikuls et al., 2006; Panchagnula et al., 2006; Pedersen et al., 2006; Pierer et al., 2006; Redaitene et al., 2006; Rodriguez-Mahou et al., 2006; Russell et al., 2006; Shankar et al., 2006; Spadaro et al., 2006; Tamai et al., 2006; vander Cruyssen et al., 2006; van der Helm-van Mil et al., 2006; Agrawal et al., 2007; Coenen et al., 2007; Forslind et al., 2007; Inanc et al., 2007; Kaltenhauser et al., 2007; Kudo-Tanaka et al., 2007; Ligeiro et al., 2007; Rantapaa-Dahlqvist et al., 2007; Turesson et al., 2007; van der Helm-van Mil et al., 2007).

RA patients can have anti-CP-positive or anti-CP-negative, anti-LCP-positive or anti-LCP-negative, anti-CCP1-positive or anti-CCP1-negative, and anti-McHale CCP2-positive or anti-CCP2-negative phenotypes. In RA patients with at least one of anti-citrullinated antigen, 78% have anti-CP and anti-CCP2 antibodies, 30% have anti-LCP and anti-CCP2, 73% have anti-CCP1 and anti-CCP2; and 12-32% have only anti-CP, 3% have only anti-LCP, 4-19% have just anti-CCP1, and 21-29% have just anti-CCP2. Patients with RA contain at least one of three anti-CP i.e. AFA, AKA and APA, 59% have concordant for all three antibodies, 25% overlap two antibodies, and 18% have only one antibody. About 5% of the statues of anti-CCP2 were changed during 3 years antirheumatic treatment in patients with RA: 2% from negative to positive and 3% from positive to negative. The frequencies of antibodies to citrullinated CapZalpha-1 were 53.3% in RA group, and 36.7% in the RA group where the antigen was non-citrullinated. Antibodies to citrullinated CII were detected in 78.5% of serum samples from 130 RA patients. Antibodies to native non-citrullinated CII were detected in 14.6% of serum samples, all of which were positive for anti-citrullinated CII. The IgG subclass profiles of antibodies against citrullinated fibrinogen in patients with RA are 61% for IgG1, 34.8% for IgG1+IgG2, IgG1+IgG3, or IgG1+IgG4, and 4.2% for IgG1+IgG2+IgG3, IgG1+IgG2+IgG4, or IgG1+IgG3+IgG4. Despite their more specific association with RA, antibodies against citrullinated antigen do have a remarkable variability in the reactive pattern towards different Cit-containing antigen. Anti-citrullinated antigen antibodies are not equivalent as diagnostic markers in patients with RA.

Detection of antibodies against citrullinated antigen has led to a definitive diagnosis of RA up to 14 years before onset of the first disease symptom. The antibodies appear to be highly predictive of the future development of RA in both healthy subjects and patients with undifferentiated arthritis. The activity of antibodies against citrullinated antigen is associated with upregulation of proinflammatory cytokines. The phenotype of RA patients with or without these antibodies is similar with respect to serological parameters of disease activity (CRP, ESR, and WBC) and clinical presentation, but differs with respect to disease course. Patients with at least one of these antibodies have a high predictive value for the development of persistent RA, worse clinical disease, more swollen joints, great radiological progression and joint destruction, severe bone lesions, mortality risk, and demand more effective antirheumatic treatment. Anti-CCP2 test identified more patients with joint damage progression than anti-LCP and anti-CCP1 test. Anti-CP but not anti-CCP2 had best predicted severity in patients with recent-onset or early polyarthritis. Anti-citrullinated antigen antibodies are not equivalent as prognostic markers in patients with RA.

A number of studies have examined the effects of active RA treatments on the serum levels of antibodies against citrullinated antigen. The doses of the antibodies was found as a stable phenotype that remained essentially unchanged after diagnosis and initiation with DMARDs, biological or biological combined DMARDs therapy, as well as clinical and remission progression. RF, but not the antibodies, were associated with clinical treatment efficacy indicating there are two independent autoantibody systems in RA. These results are in contrast to those that found active therapy by biological TNFα blockers including infliximab, adalimumab and etanercept, or by these blockers combined with DMARDs methotrexate resulted in clinical improvements to reflect significant declines in levels of anti-CCP2. BLyD therapies brought clinical responses in responding patients and were correlated with a great decrease in the levels of anti-CCP2. Nonresponding patients did not present any significant variation in anti-CCP2 levels. Antibodies to citrullinated antigen are thought to play an important role in RA pathogenesis.

The DRB1 SE alleles have been suggested to be associated with antibodies against CCP2 and predict severity in RA. Citrullinated peptide featured a high-affinity peptide interaction with HLA-DRB1 alleles. Anti-CCP2-positive RA was exclusively associated with HLA-DRB 1, and anti-CCP2-negative RA was exclusively associated with HLA-DR3. High titres of anti-CCP antibodies were significantly associated with the presence of HLA-DRB1 04/10. Data from a large number of fibrinogen peptides in both native and citrullinated forms, however, found that citrullination was not a prerequisite for binding of peptide to HLA-DR-associated alleles, and citrullinated fibrinogen peptides did not stimulate T cell proliferation more efficiently than their native forms. HLA-DRB1 alleles are most likely associated with anti-CP production because these alleles promiscuously bind fibrinogen peptides. Fifty-five percent of the sera from SE-negative RA patients were positive for anti-citrullinated fibrinogen. Expression of HLA-DRB 1 is not mandatory in order for RA patients to develop antibodies against citrullinated fibrinogen.

If citrullination of self protein is a critical step leading into breakdown in immunological tolerance, the neoepitope created on CP must be more convincingly native and decisive than the epitope mimicked by LCP, CCP1 and CCP2. However, not all proteins harboring Arg residues become reactive with anti-CP after efficient in vitro citrullination. Among 71 15-mer citrullinated fibrin-derived peptides, only 19 of them were specifically recognized by anti-CP. None of immunoreactive CP bears all the epitopes targeted by anti-CP, anti-LCP, anti-CCP1, and anti-CCP2. The sensitivity in detection of RA by anti-CP is distinctively lower than the sensitivity detected using anti-LCP, anti-CCP1 and anti-CCP2 (46% versus 48%, 53% and 66%), but all of them are extremely specific (~100%), indicating the presence of citrullinated moiety in an antigen is crucial but not sufficient. Patients with anti-CCP2-positive bore citrullinated epitopes with features predictive of the development of severe RA, and in contrast, patients with anti-CCP2-negative bore native epitopes with features predictive of less severe RA. AFA was reacted with the uncitrullinated filaggrin as an antigen and its titer was correlated with clinical parameters in patients with RA. These studies have shown that not all CP/LCP/CCP1/CCP2, nor uncitrullinated proteins/peptides equally react with antibodies against citrullinated antigen. RA-specific antibodies are anti-hapten antibodies, and the hapten is consisted of Cit and non-Cit residues on linear rather than conformational basis. Interrelation between Cit and non-Cit residues and surrounding other AA residues may determine the visibility of Cit residue, non-Cit residue or both Cit and non-Cit residues on an antigen, resulting in variable anti-citrullinated antigen-positive or anti-citrullinated antigen-negative phenotypes in patients with RA.

A chemical composition with limited mass (MW usually less than 1000) is defined as a hapten that does not elicit antibody formation when introduced into a host animal. But, when it covalently couples to a high molecular weight carrier, the resultant hapten-carrier conjugate could elicit in the host animal the formation of antibodies that recognizes the hapten. Posttranslational modification could make protein with acquired autoimmunity via adding autoepitope and elicit antibody against that neoepitope which was created. If the autoepitope is a hapten as small as Cit residue (MW 157.20) it is unlikely that it could completely occupy an entire antigen-binding site of the antibody. The bridge group that protein used to connect hapten could become an additional antigenic part other than the hapten to form the neoepitope and bind the antibody. If the neoepitope was contaminated from an incorrect bridge group, that interference could result in underestimation or overestimation of the antibody. Bridge group recognition is a general property of anti-hapten antibodies having a profound effect on sensitivity and specificity in assays using hapten-carrier as antigen. Encoding the linear epitope recognized by RA-specific antibodies will determine whether Cit, non-Cit AA, Cit residue, non-Cit AA residue, bridge group, or some combination thereof contribute to the overall binding requirements of the epitope.

Major challenges in the diagnosis and treatment of RA remain. Key issues include:

1) The lack of immunogenicity of CP to the immune system. In contrast to antibodies against CP, which have an impressive specificity of nearly 100% in RA patients and <1% of the population develops the antibodies, the presence of CP are not specific for RA but rather are a result of inflammation in everyone's life. Immunity against CP does not cause RA in experimental animal models. Does it suggest there is a process with inclusive citrullination involved in the initiation or perpetuation of autoimmunity or merely reflects ongoing inflammation that has yet to be discovered? Does it imply there is a Cit-containing autoantigen that has yet to be discovered?

2) The insufficient antigenicity of citrullinated antigens with existing antibodies. The sensitivity of antibodies to citrullinated antigens is detected in 46-66% of patients with RA. Does this imply that a considerable proportion of patients with RA do not produce anti-citrullinated antigen antibodies or are current capture antigens simply unable to detect them because of incomplete antigenicity?

3) The insufficient diagnostic accuracy of antibodies against citrullinated antigens. RA-specific antibodies to citrullinated antigens are highly specific but less sensitive. Does this indicate that Cit residue is the epitope's decisive component responsible for detection of antibodies against citrullinated antigens positive RA? If so, what is the epitope's decisive component responsible for the detection of antibodies against citrullinated antigens negative RA?

4) Considering a proportion of patients with RA do not harbor anti-citrullinated antigens antibodies, does this indicate that the presence of the antibodies is not obligatory for the development of RA or that the pathogenic mechanisms underlying anti-citrullinated antigen-positive RA and anti-citrullinated antigen-negative RA are different?

5) Considering CCP2 is moderately sensitive and detects a different subgroup of antibodies than CCP1, LCP and CP, does this indicate that the presence of bridge group recognition could result in citrullinated antigen being "visible" or "invisible" for existing specific antibodies, and does this imply that at least part of the anti-citrullinated antigen-positive were ill-defined anti-citrullinated antigen-negative, and anti-citrullinated antigen-positive and -negative do not belong to two independent development processes?

6) What is the antigen responsible for the generation of immune response against the citrullinated antigens? Mapping RA-specific antibodies-targeted epitope is important and could lead to elucidate the corresponding antigen puzzle.

7) The relationships between specific antibodies production and severe outcomes or therapeutic response in the disease.

8) How, when, where and why is the responsible break in immune tolerance generated? Does the immunity cause arthritis in animals?

9) The safety and efficacy of expensive new biological therapies.

10) Is BLyD a way to treat RA? Selectively depleting B cells involved in RA may be beneficial, as this would prevent production of RA-specific antibodies.

11) If RA-specific antibodies are involved in the pathogenesis of RA, does this imply that the antigen-specific interventions could prevent chronic arthritis and long-term joint destruction without the side effects associated with today's treatment regiments?

12) Thiol-dependent cathepsins are potential targets for RA therapeutic development. What is the thiol moiety responsible for the development or treatment of RA?

More valuable information may come from follow-up studies on the composition of the citrullinated epitope responsible for the specific occurrence of the autoantibody, the new rheumatoid factor in RA sera. If autoantibody-based classification of early RA represents the subtypes of RA that reflect incomplete epitope being harbored in antigenic substrates, analyses of the molecular basis of their antigenicity could ultimately lead to identifying what antigenic elements participated in the unelucidated epitope. If these individuals belong to a critical mutated neoepitope, it could become a platform for generation of an absolutely sensitive and specific RA test. If the epitope detected antibodies can be confirmed to be associated with the development of the disease, tremendous insight to aid diagnostic and therapeutic strategies of RA in clinical practice would be realized.

DESCRIPTION OF THE PRIOR ART

U.S. Pat. No. 7,022,485 is directed toward a citrulline polypeptide derived from fibrin useful for diagnosing or treating rheumatoid arthritis.

U.S. Pat. No. 5,888,833 is directed toward an antigen extracted from mammalian malpighian epithelia which are specifically recognized by the autoantibodies present in patients suffering from rheumatoid arthritis in respect of antigenic determinants in common with filaggrin and human profilaggrin, antigenic proteins of which said antigens are composed and peptide fragments thereof.

U.S. Pat. No. 6,858,438 relates to a peptide derived from an antigen comprising a filaggrin or profilaggrin fragment recognized by autoantibodies, which peptide is reactive with autoimmune antibodies from a patient suffering from rheumatoid arthritis.

The above-cited references fail to teach or suggest an antigenic determinant of a rheumatoid arthritis specific autoantibody characterized by the presence of a dipeptide epitope formed from amide-bond-forming between haptenic Cit and Cys residues.

SUMMARY OF THE INVENTION

This invention pertains to an antigen determinant, which is specifically recognized by autoantibodies present in the serum of patients suffering from RA, characterized by the presence of a dipeptide epitope formed from amide-bond-forming between haptenic Cit and Cys residues. The antigenic determinant, in accordance with the present invention is characterized by the presence of at least one such dipeptide epitope, and advantageously contains polydipeptide epitopes, with the molecular ratio of AA residues at least one Cit against one Cys. See Formulas I-III.

Accordingly, it is a primary objective of the instant invention to provide a method to develop an AA-based mapping library capable of covering and elucidating RA-specific antibody-defined linear epitopes. The mapping library is particularly useful for scanning these epitopes at the level of single AA residue and distinguishing exactly which of the AA residues were involved in the epitope's interaction with its corresponding antibodies. The epitope, compositions thereof encoding the epitope, and the deduced AA sequence of the epitope have been determined and are shown to be associated with RA-specific antibodies.

It is a further objective of the instant invention to provide an antigen determinant having specifically attractive features capable of recognizing and detecting the RA-specific antibody. In particular embodiments, the epitope detected antibody detects individuals having RA disease or at risk of developing RA disease.

It is yet another objective of the instant invention to provide the art with an immunoassay and method for its use to enable accurate, inexpensive and simple detection of RA-specific antibody in bodily fluid such as serum or synovial fluid. In particular embodiments, the capture agent is the antigen determinant which is covalently linked on a solid support surface capable of detecting the presence of RA-specific antibody. This detected antibody is then estimated using antihuman IgG conjugated with label.

It is a still further objective of the invention to provide immunoreactive forms of the dipeptide epitope that is associated with development of RA. The epitope targeted antibody is useful in methods to account for clinical and therapeutic responses in patients with RA. Therapeutic compositions bearing the epitope or a molecule containing the epitope may be useful in pharmacology to treat or prevent the disease for RA patients or pre-RA patients at risk of developing RA.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

For the purpose of the present invention, "dipeptide epitope" is understood to mean a monovalent hapten autoepitope whose sequence is that of the result of the action of native chemical ligation of any endogenous active Cys-enzyme or other active Cys-protein/peptide species having at least one active site Cys being haptenized immunogenically by coupling an active Cit containing peptide or nonpeptidic molecule.

For the purpose of the present invention, "native chemical ligation" is understood to mean a specific citrullination which is a site-directed haptenized mutagenesis by conjugation of an active Cit containing peptide or nonpeptidic molecule on the active site Cys of a natural, recombinant or synthetic enzyme, protein, peptide or nonpeptidic molecule.

The term "active Cys or active site Cys" as used in the present invention means the nucleophilic site Cys of a natural, recombinant or synthetic enzyme, protein, peptide or nonpeptidic molecule.

The term "active Cit" as used in the present invention means the electrophilic Cit containing peptide or nonpeptidic molecule.

For the purpose of the present invention, "antigens" may for example be produced by the action of native chemical ligation on natural, recombinant or synthetic enzyme, protein, peptide or nonpeptidic molecule, or by chemical synthesis by directly incorporating one or more dipeptide epitopes into the synthesized antigen, in the absence or presence of various amounts of neutral binding AA residue or neutral binding AA residue mimics.

DETAILED DESCRIPTION OF THE INVENTION

Definitions

Figure 1:
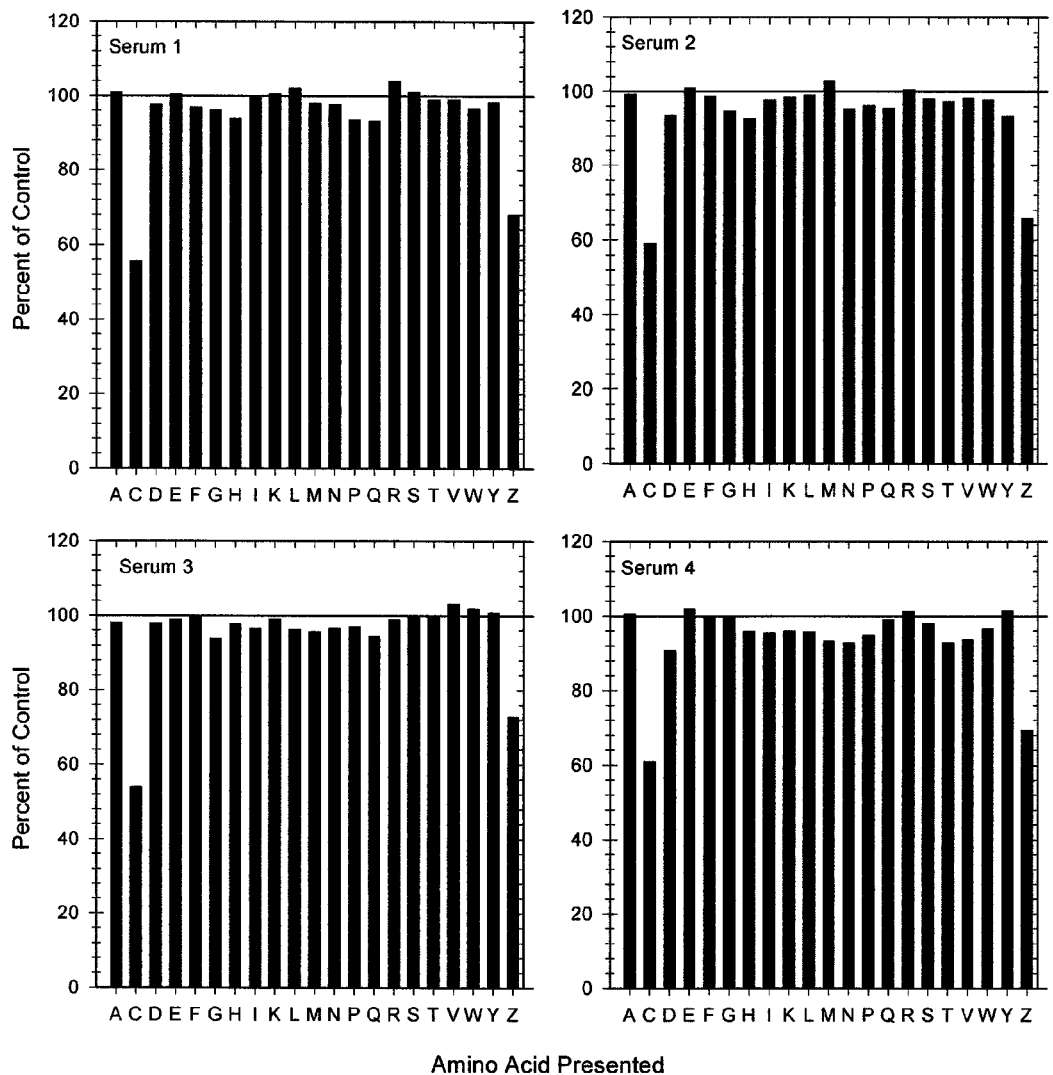
FIG. 1 shows epitope mapping of the antigenic determinant recognized with RA-specific antibodies illustrating the reactivity of each of the naturally occurring 20-coded AA and 1-noncoded Cit with sera obtained from patients suffering from RA.

"Posttranslational modification" is the chemical modification of a protein after its translation. It is one of the later steps in protein biosynthesis for many proteins. "Posttranslational modification," as used herein, refers to an introducing of other chemical groups into the makeup of an antigenic determinant on self-protein.

The term "autoimmunity" refers to the situation where autoantibodies or lymphocytes mistakenly attack molecules, cells, or tissues of the organism producing them; this can have pathological consequences leading to autoimmune disease. For example: rheumatoid arthritis, systemic lupus erythematosus, and type 1 diabetes.

The term "antibodies" as used herein refer to "autoantibodies" that are serum immunoglobulins formed against a normal body substance of the individual producing it; antibodies are generally defined in terms of their specific binding to the substance.

The term "antigen" refers to any foreign material which can induce an immune response in a mammal and be specifically bound by specific antibodies or specific lymphocytes. Antigens may also be immunogens if they are able to trigger an immune response, or haptens if not. The term "autoantigen" refers to an antigen that, despite being a normal tissue constituent, is the target of a humoral or cell-mediated immune response, as in autoimmune disease. The term "artificial antigen" refers to an antigen which is made artificially and which does not exist in nature.

The term "hapten" refers to a substance that has the property of antigenicity but not immunogenicity. Haptens are small molecules that could not induce an immune response when administered by themselves, but can when coupled to a large carrier such as a protein; the carrier also may not elicit an immune response by itself. The antibody developed against the hapten-carrier can be detected with the free hapten, the modified hapten or the hapten conjugated to adjacent residues. "Monovalent hapten," as used herein, refers to a hapten having only one site of attachment. "Capture antigen", as used herein, refers to a combination of a monovalent hapten that is covalently bound on the surface of a solid support as an antigen substrate.

The term "epitope" as used herein refers to the collective features of a molecule, such as primary structure, and charge, that together form a region on an antigen at which an antibody binds, by virtue of the antibody's antigen-binding site (called the paratope). An epitope can be either defined as a set of amino acid residues that are close together in the primary sequence of the protein, or of amino acid residues which are well separated in the primary sequence, but are brought together as a result of the natural folding of the protein to its native, fully functional shape. Epitopes consisting of residues close together in the primary sequence are called contiguous, continuous, sequential or linear epitopes, whereas epitopes consisting of residues separated in the primary sequence are by contrast called discontinuous, conformational or "assembled" epitopes.

Epitopes are present in nature, and can be mapped, isolated, purified or otherwise prepared/derived by humans. For example, epitopes can be prepared by isolation from a natural resource, or they can be synthesized in accordance with standard protocols in the art. One of these methods is the use of synthetic fragments (peptides) of the protein antigen, which can be similar enough to the homologous parts of the whole antigen to permit binding by the antibody. The affinity of the antibody for the epitope must be such that the antibody/peptide complex does not dissociate significantly under the conditions of an immunoassay. This situation occurs with linear epitopes, thus allowing the use of peptides to define those epitopes, and the use of amino acids and amino acid mimics to define individual epitopes. A derived/prepared epitope can be an analog of a native epitope. Throughout this disclosure, the terms epitope and hapten are often used interchangeably.

The term "autoepitope" refers to a portion of an autoantigen that is the specific target of an autoimmune response. The "epitope" refers to a pattern of residues in an amino acid sequence of designed peptide about 4 to about 8 amino acids in length. The combining site of an antibody will accommodate an antigenic determinant of approximately 4-8 residues.

Every amino acid has a common structure, in which a central carbon is covalently bonded to an amino group ($NH_2$), a carboxyl group (COOH), a hydrogen, and a variable sidechain "R". The term "residue" refers to an amino acid residue (—NHCHRCO—) which formed from an amino acid once a molecule of water has been lost (an H+ from the nitrogenous side and an OH— from the carboxylic side) in the formation of a peptide bond or a peptide bond mimic.

A "negative binding residue" or "deleterious residue" is an amino acid residue or amino acid residue mimic which, if present at a certain position in an epitope, results in decreased binding affinity of the epitope for the corresponding antibody.

A "neutral binding residue" is an amino acid residue or amino acid residue mimic which, if present at a certain position in an epitope, results in unchanged binding affinity of the epitope for the corresponding antibody.

A "positive binding residue" is an amino acid residue or amino acid residue mimic which, if present at a certain position in an epitope, results in increased binding affinity of the epitope for the corresponding antibody.

A "false positive binding residue" is an amino acid residue or amino acid residue mimic which, if present at a certain position in an epitope, results in increased binding affinity of the epitope for the corresponding antibody, when in fact it is not considered as a composition derived from the epitope.

The term "spacer" is understood to mean a spacer or linker molecule which occurs between separate positive binding residues to permit them to be linked covalently into an antigen determinant. The spacer molecule is preferably of neutral binding residue. The spacer molecule may be, for example, amino acid residue, amino acid residue mimic, and combination thereof. The spacer may be the same molecule type as Cit or Cys. The spacer molecule can be attached to the positive binding residues by, for example, an amido linkage or alternatively by ester bonds, imine bonds, or combinations thereof.

A "primary anchor residue" is an essential positive binding residue at a specific position along a peptide sequence which is understood to provide a contact point between the immunogenic peptide and the antibody, one, two, or three, positive binding residues within a peptide of defined length generally defines an "epitope" of immunogenic peptide. These residues are understood to fit in close contact with antigen binding sites of the antibodies, with their sidechains buried in specific pockets of the binding sites themselves.

The "native" sequence refers to a sequence found in nature.

The term "analyte" refers a chemical component to be determined or measured.

The term "cross-reactivity" refers to the ability of an antibody, specific for one antigen, to react with a second antigen; a measure of relatedness (%) between two different antigenic substances based on the IC50 values (moles of the analyte that give 50% displacement of bound antibody).

The term "sensitivity" of a test refers to the proportion of true positives it detects of all the positives. It is thus a measure of how accurately it identifies positives. All positives are the sum of (detected) true positives (TP) and (undetected) false negatives (FN). Sensitivity is therefore: TP/(TP+FN)×100%.

The term "specificity" of a test refers to the proportion of true negatives it detects of all the negatives. It is thus a measure of how accurately it identifies negatives. All negatives are the sum of (detected) true negatives (TN) and (misdiagnosed) false positives (FP). Specificity is therefore: TN/(TN+FP)×100%.

The term "detecting" or "detection" refers to qualitatively or quantitatively determining the presence of the biomolecule under investigation.

The complete set of amino acids refers to the 20-coded naturally occurring amino acids and 1-noncoded naturally occurring Cit.

The nomenclature used to describe epitope compounds follows the conventional practice wherein the amino group is presented to the left (the N-terminus) and the carboxyl group to the right (the C-terminus) of each amino acid residue. The α-form of an amino acid residue is represented by a capital single letter or a capital first letter of a three-letter symbol. Citrulline has no letter symbol yet and is simply referred to as "Z" or "Cit".

Standard symbols/nomenclatures for a amino acids are shown below: Single Letter Three Letter Symbol Amino Acids: A Ala Alanine; C Cys Cysteine; D Asp Aspartic Acid; E Glu Glutamic Acid; F Phe Phenylalanine; G Gly Glycine; H His Histidine; I Ile Isoleucine; K Lys Lysine; L Lieu Leucine; M Met Methionine; N Asn Asparagine; P Pro Proline; Q Gln Glutamine; R Arg Arginine; S Ser Serine; T Thr Threonine; V Val Valine; W Trp Tryptophan; Y Tyr Tyrosine; Z Cit Citrulline.

Acronyms used herein are as follows:
AA: Amino acid; ACR: American College of Rheumatology; AFA: Antifilaggrin antibodies; AKA: Antikeratin antibodies; APA: Antiperinuclear factor; Be: Butyl ester; BLyD: B lymphocyte depletion; BSA: Bovine serum albumin; CP: Citrullinated endogenous protein/peptide; CCP: A single cyclic citrullinated peptide; CCP1: CCP-derived from filaggrin sequences formed first generation RA test; CCP2: Artificial CCPs with no homology with filaggrin or other known proteins formed second generation RA test; CRP: C-reactive protein; CT: C-terminal; DMARDs: Disease modifying antirheumatic drugs; EBV: Epstein-barr virus; Ee: Ethyl ester; ELISA: Enzyme-linked immunosorbent assay; ESR: Erythrocyte sedimentation rate; IP: Interstitial pneumonia; LCP: Short linear citrullinated peptide; McAb: Monoclonal antibody; Me: Methyl ester; MHC: Major histocomptibility complex; MW: Molecular weight; NO: Nitric oxide; NOS: Nitric oxide synthase; NT: N-terminal; PAD: Peptidylarginine deiminase; PADI2: Isotype 2 of PAD; PADI4: Isotype 4 of PAD; PBST: Phosphate buffered saline tween-20; PcAb: Polyclonal antibody; Pe: Propyl ester; RA: Rheumatoid arthritis; RF: Rheumatoid factor; SE: Shared epitope; TMB: 3,3',5,5'-Tetramethylbenzidine; TNFα: Tumor necrosis factor α; WBC: White blood cell count.

At present there is a lack of knowledge regarding the native sequence of the epitope under study. This has prevented any interpretation as to why antibodies against citrullinated antigens have low sensitivity at high specificity and contradictory clinical and laboratory responses to the pharmacological treatments when applied as RA diagnostic and prognostic marker.

Cit is a non-code amino acid showing very similarly chemical structures with Arg, differing only in the neutral ureido group instead of positively charged guamido group. Cit has been reported to be an essential constituent of epitopes recognized by RA-specific antibodies. Our unpublished epitope mapping studies find that Cit does not bind any RA-specific antibodies but Cit's residue does. The reactivity was higher in derivatized Cit containing both conjugated amino and carboxy groups than in derivatized Cit containing either conjugated amino or carboxy group alone.

The existences of antibodies to citrullinated antigen in patients with RA, and Cit residue as part of the antibodies recognized epitope, are two primary requisites that open up the prospect of accurately encoding the hitherto poorly understood epitope.

Mapping RA-specific antibodies-targeted epitope was investigated by determining cross-reactivities with each of 21 α-amino acids including 20 coded and 1 non-coded Cit, and their derivatives that represent counterpart residue variants possibly existed in the epitope. These analytes were described by 3-point pharmacophore model to represent structural features importance to antibodies binding. Point 1 is an amino (—NH₂) functional group attached to the α-carbon, or analogs thereof at the α-NH₂. Point 2 is a carboxylic acid (—COOH) attached to the α-carbon, or analogs thereof at the α-COOH. Point 3 is distinct sidechain R attached to the α-carbon. Three-point analyses of analytes cross-reactivities could provide more sensitive and specific means to define what amino acid residues participate in the epitope and what amino acid sequence exist in the epitope.

The invention is directed toward an antigenic determinant for RA characterized as being reactive with at least one rheumatoid arthritis (RA)-specific autoantibody comprising:

a dipeptide sequence including at least one α-Cit residue and at least one α-Cys residue according to Formula III;

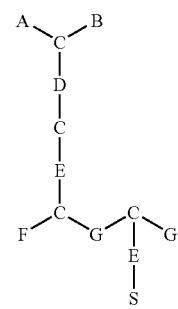

wherein said α-Cit residue is a haptenic moiety having the Formula I

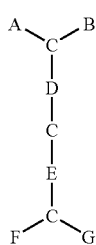

in which A is NH$_2$; B is —O—; D is —NH—; F is —NHCO—, or —NR—, wherein R is hydrogen or acyl; G is —CONH—, or —COOR, wherein R is alkyl; and E is (CH$_2$)$_{n'}$, wherein n' is an integer from 1 to 6;

wherein said α-Cys residue is a haptenic moiety having the Formula II

in which S is —SH or SS when free thiol (SH) of α-Cys is crosslinked by way of a disulfide bond to another α-Cys; F is —NHCO—, or —NR—, where R is hydrogen or acyl; G is —CONH—, or —COOR—, wherein R is alkyl; and E is (CH$_2$)$_{n'}$, wherein n' is an integer from 1 to 6;

whereby an artificial antigen composition is provided which functions as an antigenic determinant for RA.

The invention is further directed toward a process for producing an antigenic determinant for RA characterized as being reactive with at least one rheumatoid arthritis (RA)-specific autoantibody comprising:

carrying out cysteine ligation through thioester capture by thiol-thioester exchange involving a C-Terminus-Cit thioester as an electrophile and an N-Terminus-Cys as nucleophile, which ligation results in the formation of a citrullinated cysteine-containing peptide between two peptide segments having Formula III:

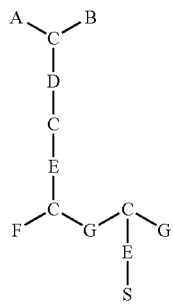

wherein said α-Cit residue is a haptenic moiety having the Formula I

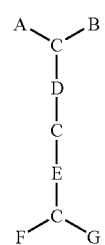

in which A is NH$_2$; B is —O—; D is —NH—; F is —NHCO—, or —NR—, wherein R is hydrogen or acyl; G is —CONH—, or —COOR, wherein R is alkyl; and E is (CH$_2$)$_{n'}$, wherein n' is an integer from 1 to 6; and wherein said α-Cys residue is a haptenic moiety having the formula II

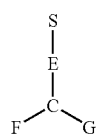

in which S is —SH or SS when free thiol (SH) of α-Cys is crosslinked by way of a disulfide bond to another α-Cys; F is —NHCO—, or —NR—, where R is hydrogen or acyl; G is —CONH—, or —COOR—, wherein R is alkyl; and E is (CH$_2$)$_{n'}$, wherein n' is an integer from 1 to 6.

With regard to the above-described antigen determinant it is contemplated that the autoantibody is involved in the pathogenesis of RA disease and said formation of an antigen/antibody complex is indicative of the presence of RA-specific autoantibody and is diagnostic of RA.

In a particular embodiment an artificial antigen comprising at least one Cit residue and one Cys residue is connected by means of a spacer T$_{n'}$, wherein n' is an integer from 1 to 6 resulting in an antigenic determinant having Formula IV:

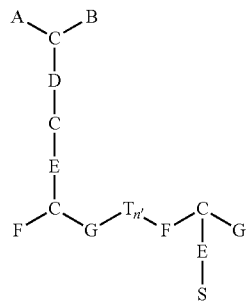

In another embodiment, an artificial antigen N-Terminus-Cys is connected by one or more Cits resulting in an antigenic determinant having the Formula V:

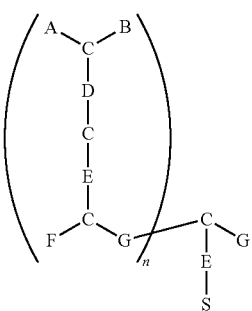

V

In yet another embodiment, an artificial antigen N-Terminus-Cys is connected by one or more Cits by means of a spacer $T_{n'}$, resulting in an antigenic determinant having the Formula VI:

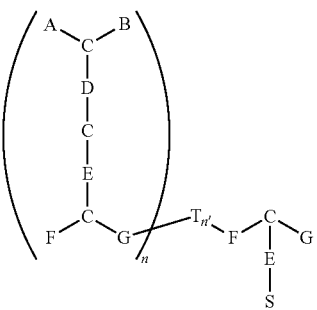

VI

In still another iteration, the artificial antigen N-Terminus-Cys is connected by one or more Cits by means of a spacer $T_{n'}$ including at least one Cys in that the antigen determinant is having the Formula VII:

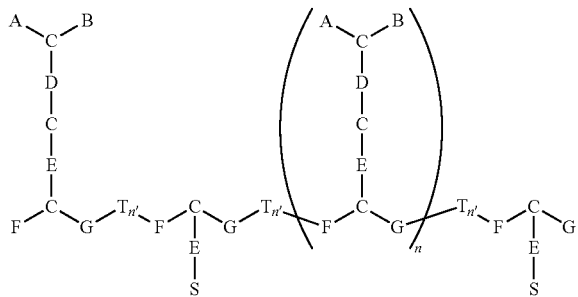

VII

It is contemplated that in accordance with the instant invention, the antigenic determinant may be an artificial antigen which is coupled to a carrier molecule. Furthermore, the artificial antigen may be immobilized either covalently or noncovalently on a solid phase support. Additionally, the artificial antigen may be labeled.

It is further contemplated to provide a pharmaceutical composition comprising a peptide sequence in accordance with the present invention in combination with a pharmaceutically acceptable carrier. The pharmacologically acceptable carrier is provided in the form of pharmaceutical preparations suitable for oral or parenteral administration, its salt, a diluent or excipient.

In accordance with the present invention, it is further contemplated to provide a monoclonal antibody or a polyclonal antiserum comprising antibodies that specifically binds to at least one haptenic moiety presented by a dipeptide sequence as illustrated herein; additionally provided are an enzyme-linked immunosorbent assay (ELISA) kit for conducting an RA test to determine presence of RA-specific autoantibody comprising: a) at least one antigen having a formula selected from Formulas III-VII immobilized on a solid phase support as a capture antigen, whereby contacting said autoantibody in a biological sample with said capture antigen and incubating a labeled antihuman IgG with said autoantibody attached by said capture antigen results in a determination of the presence of said autoantibody wherein diagnosis and severity of RA is determined, and a sandwich ELISA kit for determining presence of an RA specific autoantibody comprising a monoclonal or polyclonal antibody which binds to at least one antigen selected from Formula I-VII immobilized on a solid phase support as capture antibody; whereby reacting said autoantibody in a biological sample as a reporter antibody with said antigen attached by capture antibody followed by incubating a labeled antihuman IgG with said sandwich formed from said reporter antibody and said antigen and said capture antibody results in detection of RA and the dose change of said reporter antibody determines severity of RA.

The invention will now be explained in more detail by means of the following example.

Preparation of Amino Acid Derivatives

Linear epitope recognized by B cells and the antibodies secreted by B cells are created by the primary sequence of amino acids in the peptide that begins with the amino of the first AA and continues to the carboxyl end of the last AA with a peptide bond existing between two AA residues.

To insure that the linear epitope was investigated at the level of single AA residue, amino acids were derivatized by adding an acetyl group at point 1, or adding an alkyl group at point 2, or adding acetyl and alkyl groups at point 1 and 2 with known protocols (See, e.g., Herrera-Marschit & Leibach & Lubec, Amino Acids, ISSN: 0939-4451, Springer Wien, 2004).

The amino acids, and the derivatizing reagents used to perform AA acetylation and alkylation can be purchased from chemical suppliers such as Sigma Chemical Company (St Louis, Mo.). The AA derivatives were at least 95% pure, as determined by reversed-phase high-performance liquid chromatography. The composition of the derivatized AA was confirmed by the means of gas chromatography-mass spectrometry (GC-MS).

Epitope Compositions

Linear epitope compositions, in accordance with the present invention, which recognize RA-specific antibodies, were examined by determination of cross-reactivities via indirect ELISA using immobilized CCP2 as a capture antigen (Immunoscan RA, Cat RA-96, Lot FS 2900), and 4 positive sera including 1 from Eurodiagnostic (Immunoscan RA, Cat RA-96, Lot FS 3166) and 3 from anti-CCP2-positive RA patients, as detector antibodies. A complete set of 21 amino acids and their derivatives were used as analytes to determine if any analyte inhibited the action of the detector antibody in binding to the capture antigen. Determination was made by observation at the single AA level through a series of moving windows of different derivatization. Following this procedure ensures that no antigenic elements of the epitope are missed as long as the possible AA derivatives are available. The analysis began in the fluid phase, wherein initially, the detector antibody was incubated with each of the analytes. After overnight incubation at 4° C., 100 µl of analyte preadsorbed detector antibody per well were added into 96-well microplate which immobilized CCP2 on the surface, and was incubated for 1 hour at room temperature with shaking. The plate was then emptied, washed 5 times with washing buffer, followed by addition of 100 μl of peroxidase conjugated anti-human IgG (Immunoscan RA, Cat RA-96, Lot FS 3165) i.e. reporter antibody per well, and incubated on shaking for 1 hour at room temperature. After emptying and washing out any unbound materials, 100 μl of peroxidase substrate TMB (Immunoscan RA, Cat RA-96, Lot FS 3156) per well was added and incubated for 30 min at room temperature under darkness. The reaction was stopped by adding 100 μl of 0.5 M H2SO4 per well and the results were estimated at A450 nm.

The concept of indirect ELISA was based upon an inhibition test between an unknown amount of analyte and a known amount of immobilized antigen for a limited number of detector antibody binding-sites. If the contents of detector antibody and immobilized antigen are kept constant, the distribution of detector antibody between immobilized antigen bound detector antibody and analyte bound detector antibody is dependent upon the amount of sample analyte. The mass of immobilized antigen bound detector antibody is inversely proportional to the amount of analyte bound detector antibody. An analyte was thus considered a composition of the epitope when its presence resulted in at least a 70% decrease in the binding interaction of the antibody with the CCP2. On the contrary, residues not considered a composition derived from the epitope could not give this interaction. Indirect ELISA thereby provides precise information concerning the composition of the linear epitope recognized by RA-specific antibodies.

As described in FIG. 1, Amino Acid Profiles for the Antigenic Determinant, ELISA was carried out with sera from Euro-diagnostica (serum 1) and from three patients (serum 2, 3, and 4) with RA to CCP2 positive at various concentrations of different amino acids. Each bar represents the capacity of that AA found at 50 mM in inhibition of antibody binding to the immobilized CCP2. The horizontal line at 100% represents the control percent binding of the CCP2 to the antibody.

Figure 2:
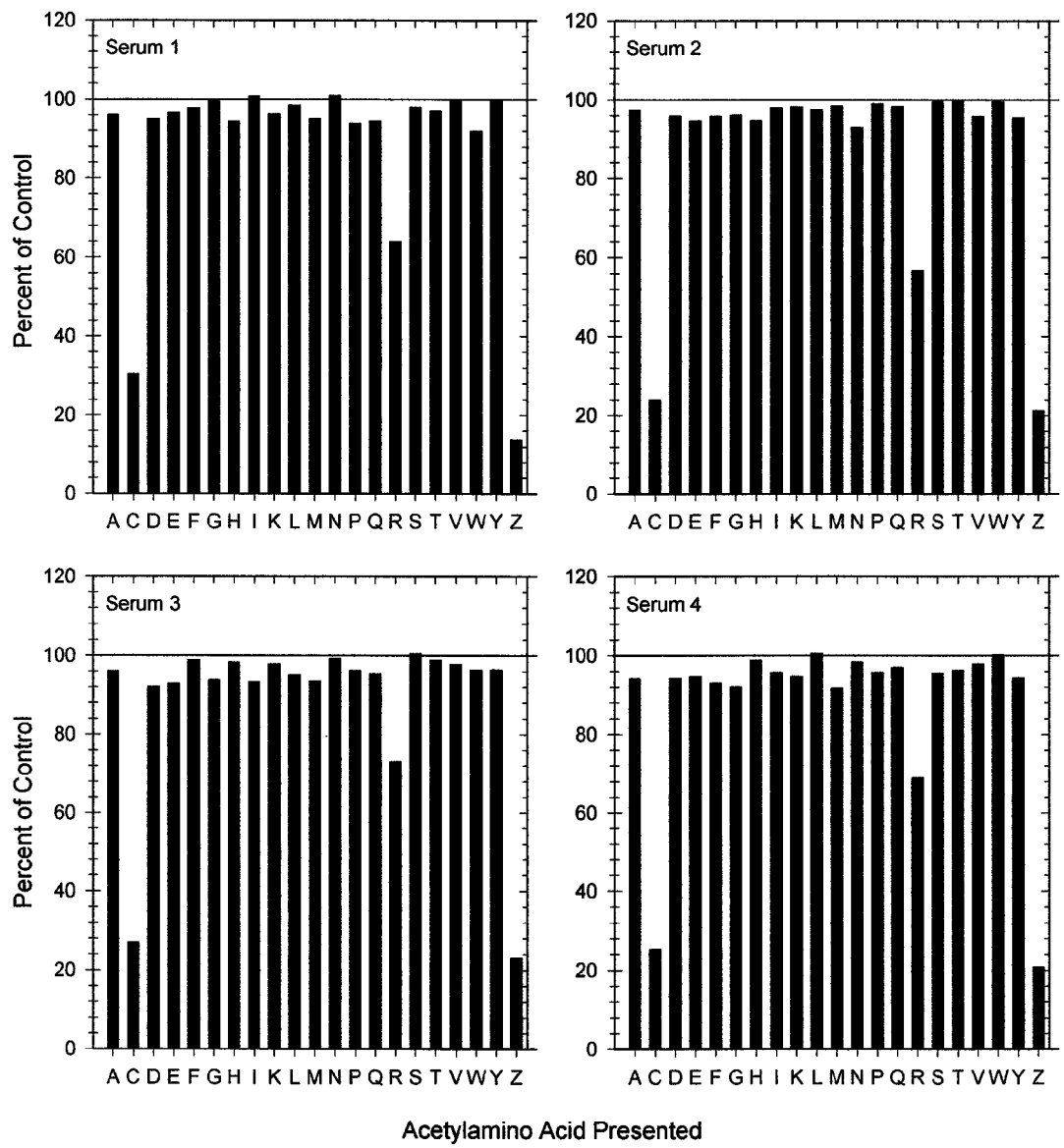
FIG. 2 shows epitope mapping of the antigenic determinant recognized with RA-specific antibodies illustrating the reactivity of each of the acetylated 20-coded AA and 1-noncoded Cit with sera obtained from patients suffering from RA.

As described in FIG. 2, Acetylamino Acid Profiles for the Antigenic Determinant, ELISA was carried out with sera from Euro-diagnostica (serum 1) and from three patients (serum 2, 3, and 4) with RA to CCP2 positive at various concentrations of different acetylamino acids. Each bar represents the capacity of that acetylamino acid found at 50 mM in inhibition of antibody binding to the immobilized CCP2. The horizontal line at 100% represents the control percent binding of the CCP2 to the antibody.

Figure 3:
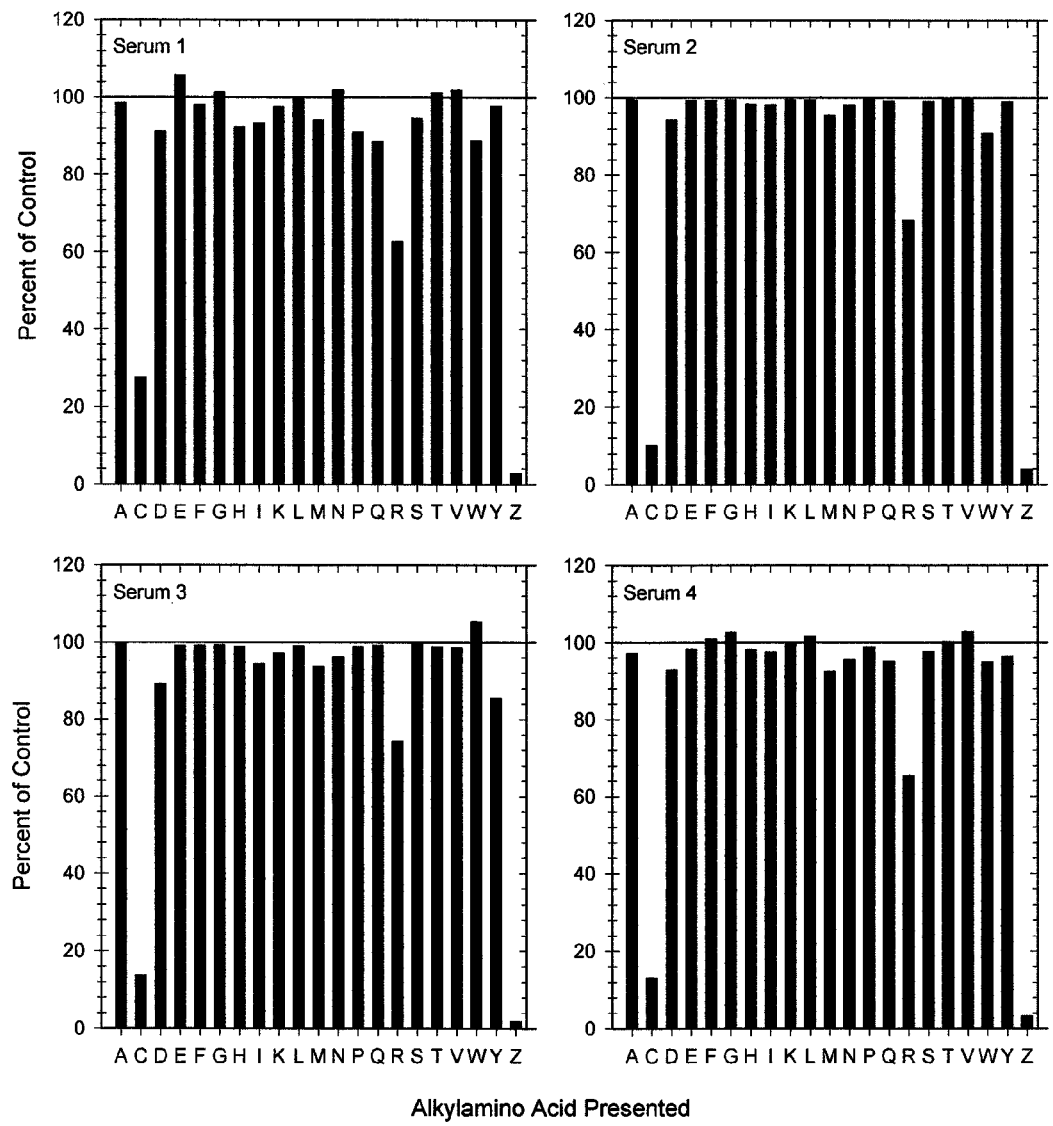
FIG. 3 shows epitope mapping of the antigenic determinant recognized with RA-specific antibodies illustrating the reactivity of each of the alkylated 20-coded AA and 1-noncoded Cit with sera obtained from patients suffering from RA.

As described in FIG. 3, Alkylamino Acid Profiles for the Antigenic Determinant, ELISA was carried out with sera from Euro-diagnostica (serum 1) and from three patients (serum 2, 3, and 4) with RA to CCP2 positive at various concentrations of different alkylamino acids. Each bar represents the capacity of that alkylamino acid found at 50 mM in inhibition of antibody binding to the immobilized CCP2. The horizontal line at 100% represents the control percent binding of the CCP2 to the antibody.

Figure 4:
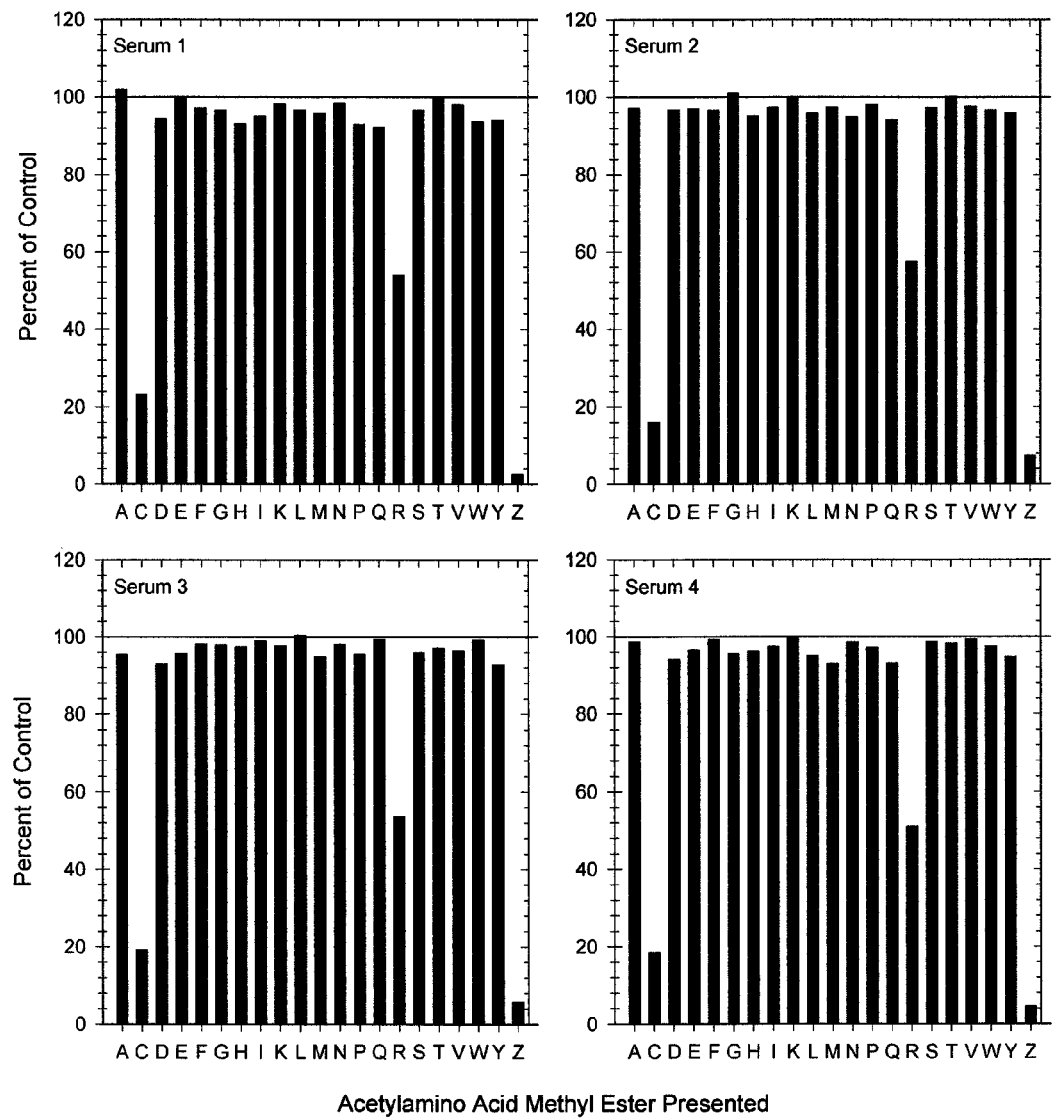
FIG. 4 shows epitope mapping of the antigenic determinant recognized with RA-specific antibodies illustrating the reactivity of each of the alkylated and acetylated 20-coded AA and 1-noncoded Cit with sera obtained from patients suffering from RA.

As described in FIG. 4, Acetylamino Acid Methyl Ester Profiles for the Antigenic Determinant, ELISA was carried out with sera from Euro-diagnostica (serum 1) and from three patients (serum 2, 3, and 4) with RA to CCP2 positive at various concentrations of different acetylamino acid methyl esters. Each bar represents the capacity of that acetylamino acid methyl ester found at 50 mM in inhibition of antibody binding to the immobilized CCP2. The horizontal line at 100% represents the control percent binding of the CCP2 to the antibody.

Figure 5:
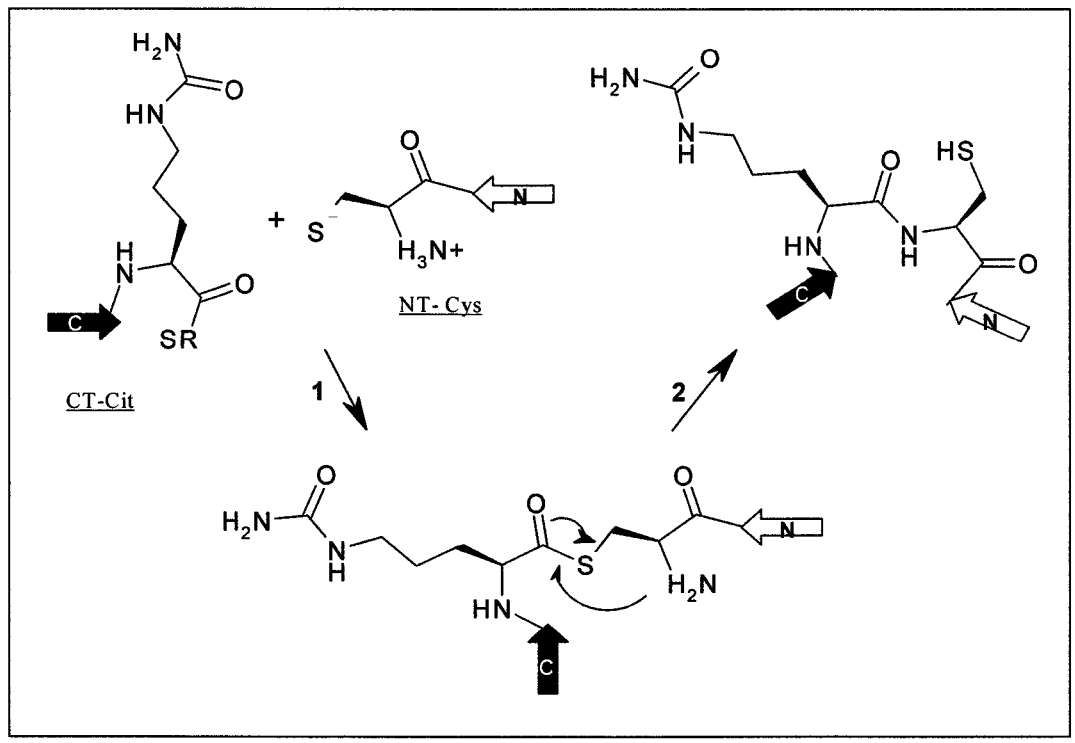
FIG. 5 is a schematic representation of citrullination of protein by native chemical ligation.
Figure 6:
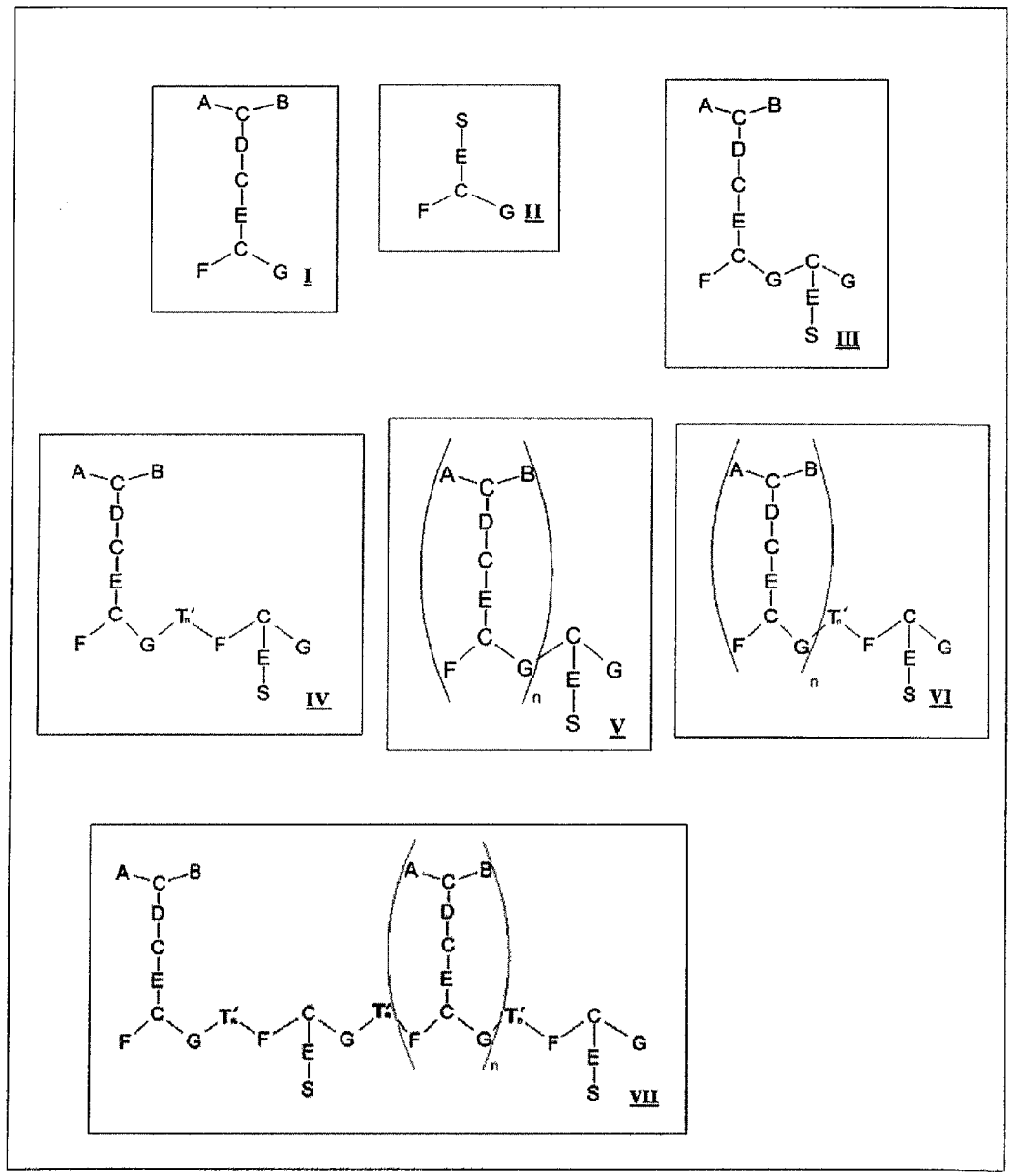
FIG. 6 is a Formula Sheet.

With reference to FIG. 5, A Schematic Representation of Citrullination of Protein by Native Chemical Ligation, CT-Cit and NT-Cys thioester represent a pair of electrophilic and nucleophilic segments. CT-Cit thioester undergoes nucleophilic attack by the thiol of NT-Cys. The initial thioester ligation product undergoes rapid intramolecular thioester-to-amide rearrangement to yield a neoepitope Cit-Cys with a native amido bond at the ligation site that leads to breakdown in immunologic tolerance of the self protein. Section 1, Chemoselective transthiolesterification; Section 2, Spontaneously intramolecular S to N acyl transfer.

As further illustrated in FIG. 1, when the analyte profiles in the assays were α-amino acids, only Cit and Cys exhibited limited capability to inhibit antibodies binding to the immobilized CCP2. All 21 amino acids are excluded from being part of the epitope. Neither coded nor non-coded amino acids represent any antigenic residue profiles in the linear epitope.

As further illustrated in FIG. 2, when the analyte profiles in the assays were acetylated α-amino acids, acetyl-Cit and acetyl-Cys gave strong inhibition, acetyl-Arg revealed limited inhibition and the remaining 18 acetylamino acids showed virtually no inhibition for antibodies binding to the CCP2. Similarly, as further illustrated in FIG. 3, trends of immunological responsiveness were recorded when the analyte profiles in the assays were alkylated α-amino acids.

As illustrated further in FIG. 4, when the analyte profiles in the assays were acetylated α-alkylamino acids, e.g., acetylated amino acid methyl esters, the mimicked amino acid residues in peptides, revealed that features between point 1 and point 2 are important for immunological recognition of Cit and Cys by the 4 antibodies. Antibodies gave 74%, 81% and 100% cross-reactivities with acetyl-Cit, Cit-Me and acetyl-Cit-Me; and 50%, 48% and 57% cross-reactivity with acetyl-Cys, Cys-Me and acetyl-Cys-Me, respectively, as set forth in Table 1.

A review of Table 1 leads to the following explanations and observations:

TABLE 1

Cross-reactivity of RA-specific Antibody with Derivatives of α-Amino Acids
Cross-reactivity (%)

| α-Amino acid | Modified α-amino acid | | |
|---|---|---|---|
| | Alkylation | acetylation | alkylation + acetylation |
| Alanine | 0 | $Me_0$ | 0 | 0 |
| Cysteine | 0 | $Me_{50}$ | 48 | 57 |
| Aspartic acid | 0 | $Me_0$ | 0 | 0 |
| Glutamic acid | 0 | $Me_0$ | 0 | 0 |
| Phenylalanine | 0 | $Me_0$ | 0 | 0 |
| Glycine | 0 | $Me_0$ | 0 | 0 |
| Histidine | 0 | $Me_0$ | 0 | 0 |
| Isoleucine | 0 | $Me_0$ | 0 | 0 |
| Lysine | 0 | $Me_0$ | 0 | 0 |
| Leucine | 0 | $Me_0$ | 0 | 0 |
| Methionine | 0 | $Me_0$ | 0 | 0 |
| Asparagine | 0 | $Me_0$ | 0 | 0 |
| Proline | 0 | $Me_0$ | 0 | 0 |
| Glutamine | 0 | $Me_0$ | 0 | 0 |
| Arginine | 0 | $Me_5$ | 6 | 13 |
| Serine | 0 | $Me_0$ | 0 | 0 |
| Threonine | 0 | $Me_0$ | 0 | 0 |
| Valanine | 0 | $Me_0$ | 0 | 0 |
| Tryptophan | 0 | $Me_0$ | 0 | 0 |
| Tyrosine | 0 | $Me_0$ | 0 | 0 |

TABLE 1-continued

Cross-reactivity of RA-specific Antibody with
Derivatives of α-Amino Acids
Cross-reactivity (%)

| α-Amino acid | Modified α-amino acid | | |
|---|---|---|---|
| | Alkylation | acetylation | alkylation + acetylation |
| Citrulline 0 | $^{Me}$81 | 74 | 100 |
| | $^{Ee}$72 | n.d. | n.d. |
| | $^{Pe}$115 | n.d. | n.d. |
| | $^{Be}$124 | n.d. | n.d. |

$^{Me}$methyl esterified;
$^{Ee}$ethyl esterified;
$^{Pe}$propyl esterified;
$^{Be}$butyl esterified;
0, cross-reactivity less then 1%;
n.d., not detected.

Arg is identical to Cit except that a guanidine group replaces an ureido group in the sidechain. Antibodies showed zero cross-reactivity with Arg and Cit. Acetyl-Arg, Arg-Me and acetyl-Arg-Me have identical sidechain as Arg, but the carboxyl and amino group at a position are acetylated or alkylated or both. Cross-reactivities of antibodies were 5%, 6% and 13% with acetyl-Arg, Arg-Me and acetyl-Arg-Me, respectively.

Met and Cys are the only sulfur-containing amino acids. Met differs from Cys by adding the methylene and the methyl replaces the hydrogen of the thiol in the sidechain. Ser is identical to Cys except that the oxygen of the alcohol replaces the sulfur of the thiol in the sidechain. Antibodies gave 0 cross-reactivity with Cys, Met, Ser, acetyl-Met, acetyl-Ser, Met-Me, Ser-Me, acetyl-Met-Me, and acetyl-Ser-Me, respectively.

The bridge group which led Cit to be antigenic via conjugation at a position was analyzed by 4 alkylated Cit derivatives. They differ from Cit in that methyl, ethyl, propyl or butyl replaces the hydrogen of the carboxy group in the molecule. Antibodies gave 81%, 72%, 115% and 124% cross-reactivities with Cit-Me, Cit-Ee, Cit-Pe and Cit-Be, respectively. The α-carbon attached ureido-containing sidechain, and either amino group, carboxy group, or both, conjugated with suitable bridge group of at least 3 carbon atoms in length, are strictly required for recognition of Cit by these antibodies.

The negligible difference in cross-reactivities between acetyl-Cys or Cys-Me and acetyl-Cys-Me indicate that Cys is a bridge group that keeps its carboxy group conjugated in a self-protein, and leaves its thiol-containing sidechain and amino group free to link to the carboxyl group of Cit to form the neoepitope. The α-carbon attached thiol-containing sidechain and both amino and carboxy groups with at least one being conjugated are strictly required for recognition of Cys by these antibodies.

Cit and Cys residues are two positive binding residues, as well as being two primary anchor residues. Arg residue is a false positive binding residue. AA residues other than the Cit, Cys and Arg are either negative or neutral binding residues.

The dipeptide neoepitope is developed when an amidation is introduced between Cit and Cys residues, which led to ureido- and thiol-containing sidechains possessing structural and electrical characteristics with antigenicity.

Cit presents the common reactivity of the α-amino acid family. In particular, it can form peptide bond; hence it can therefore be present in proteins. However, there is no experimental proof that Cit is able to incorporate with Cys into a protein during translation as there is no evidence for the existence of tRNA capable of transporting Cit with Cys.

The presence of Cit in a protein must always result from a posttranslational modification of the protein. PAD is believed to be responsible for this modification, citrullination, which is the conversion of peptideyl Arg to peptideyl Cit.

Studies with peptides indicate that types of AA residues neighboring Arg influence its susceptibility to citrullination by PAD. For example, a single Arg sandwiched between two Pro residues can not be citrullinated; and an Arg neighboring Cys crosslinked by disulfide bond to another Cys appears to be highly resistant to citrullination.

PAD, in this situation, could play no role in citrullination of Arg flanking Cys, because of the disulfide reduction of cystine, and it is uncommon to find Cys on the surface of a protein, demonstrating the existence of a process other than PAD in the formation of the dipeptide neoepitope.

Given the high activity of NOS enzyme (catalyzes the formation of NO and Cit) in inflammatory sites, the NO-dependent tissue injury in RA, the thiol-dependent transport activity of ornithine/citrulline carrier, the thiol-dependent catalytically activity of Cys protease cathepsin in antigen presentation and in joint inflammation and destruction in RA, and the altered thiol pattern in RA plasma include significantly lower levels of protein sulfhydryls and cysteinl-glycine and significantly increased cystine, homocystine, and protein-bound Cys and homocysteine, one might speculate as to some association between citrullinated antigen formation and thiol-dependent activity of such related enzymes or proteins.

The active site of these enzymes is formed by a nucleophilic thiol residue of Cys which can be easily targeted by an electrophilic moiety placed into a peptide or other structure recognized by the enzyme's substrate-binding region. The electrophilic moiety can react as a reversible or irreversible inhibitor to inactivate targeted enzyme.

Advances in the design of new therapeutics have largely focused on reversible inhibitors from low MW compounds with thiol trapping pharmacophore that are proposed to have antiarthritic activity through the active site directed inactivation of enzyme.

The general concern for irreversible inhibitors is that despite their selectivity, they have the potential drawbacks of haptenization that could cause toxin side effects or generate immunogenic haptens when reacted over time with reactive Cys-enzyme and other reactive Cys-protein species adducing covalently bound native peptide ligation.

As further illustrated in FIG. 5, it is thus logical to assume that the native peptide ligation, but not the PAD, as a unique posttranslational modification of protein, participates in the generation of the neoepitope. This process assumes that occurrence of a CT-Cit ester or thioester segment bearing electrophilic function, can react with a NT-Cys-nucleophilic segment, and is followed by an S→N acyl rearrangement that forms a native peptide bond resulting in incorporation of Cit and Cys in a linear dipeptideyl neoepitope.

Any modification over that region of the epitope, such as delocalisation of electrons by introduction of additional substitute or replacement of any one of these residues with any other amino acid could result in loss of antibody binding, or in false positive antibody binding, indicating that both are primary anchor residues together with the peptide linkage, which form the overall recognition site of the dipeptide epitope composition by RA-specific antibodies.

Preparation of Linear Dipeptide Epitope

A peptide epitope in accordance with the invention can be prepared synthetically by recombinant technology plus post-translational modification or chemical synthesis, or from natural sources such as pathogenic organisms. Peptide epitopes may be synthesized individually or as polyepitope peptides.

The epitope in accordance with the invention can be a variety of lengths, and either in their neutral (uncharged) forms or in forms which are in salts. The epitope in accordance with the invention can contain modification such as glycosylation, sideshain oxidation, or alkylation, generally subject to the condition that modifications do not affect the immunogenicity of the epitope.

The peptide epitope of the invention can be prepared in a wide variety of ways. For the preferred relatively short size, the epitope can be synthesized in solution or on a solid support in accordance with conventional techniques. Various automatic synthesizers are commercially available and can be used in accordance with known protocols. Further, individual peptide epitopes can be joined using chemical ligation to produce larger peptides that are still within the bounds of the invention.

Alternatively, recombinant DNA technology can be employed wherein a nucleotide sequence which encodes an immunogenic peptide interest is inserted into an expression vector, transformed or transfected into an appropriate host cell and cultivated under conditions suitable for expression. Thus, recombinant peptide which comprises one or more epitopes of the invention, the epitope containing Arg residue in the peptide can be enzymatically deiminated by PAD.

The linear peptide epitopes were synthesized on the basis of known composition of the dipeptide epitope (Table 1). Two polyepitope peptides, referred herein as polycitrulline CitD1 (SEQ ID No.1) and citrullinated cysteine CitD2 (SEQ ID No.2), were formed, for example, each with 21 AA. CitD1 corresponds to the N-terminus of the dipeptide epitope, Cit residue: Cit-Cit-Cit-Cit-Cit-Cit-Cit-Cit-Cit-Cit-Cit-Cit-Cit-Cit-Cit-Cit-Cit-Cit-Cit-Cit-Cit, and CitD2 to the epitope from the N-terminus, Cit and Cys residues: Cit-Cys-Cit-Cit-Cit-Cit-Cit-Cit-Cys-Cys-Cit-Cit-Cit-Cit-Cys-Cit-Cit-Cys-Cit-Cys, were synthesized by the solid-phase strategies. The purities of peptides were at least 95%, as determined by high-performance liquid chromatography. The identity of the peptides was conformed by means of amino acid sequencing and mass spectrometry. All peptides were synthesized as peptide amides.

Detection of RA-Specific Autoantibody

The method provided herein includes techniques to detect RA-specific autoantibodies capable of binding to the antigen composition described above. These methods permit detection of circulating antibodies to the dipeptide epitope in order to indicate the presence of antibodies in patients with RA and thereby diagnose RA or prognose erosive disease in individuals with developing RA or monitor the progress of therapeutic agent in treating the disease.

There are many techniques known in the art for detecting or measuring antibody-antigen complexes also referred to herein as bound antibody or immunocomplexes. Classical methods involve providing a sample containing the antibody with a known immobilized antigen specific for the antibody, separating bound from free antibody, and determining the amount of bound antibody. Anti-antibody referred herein as second antibody or reporting antibody labeled with a detectable label is used to aid in the determination of the amount of bound antibody. The label is commonly an enzyme or a fluorescent or radioactive group. The label is then detected using methods well known to those skilled in the art such as spectrophotometry, scintillation counting, or flow cytometry.

The immobilized antigen can be made by coating or covalently coupling the antigen to a solid phase such as the wells of 96-well microliter plates or bead or particle.

In a preferred embodiment, the capture antigen was covalently coupled via a peptide bond to an N-oxysuccinimide surface of the wells of 96 well immunoassay microplates (Corning, Acton, Mass.) for ELISA detection of antibodies. The antigen was dissolved in diluent (50 mmol/L $Na_3PO_4$, 1 mmol/L EDTA, pH 8.5) at a concentration of 10 µg/ml and 100 µl/well was added and performed coupling at 4° C. for 16 hours. The wells were blocked with 2% BSA in diluent for 1 hour at room temperature. Patient and normal sera as detector antibodies were diluted 1:200 with dilution buffer containing 0.05% Tween-20, 1% BSA and 10% FBS in PBS (10 mmol PB, 300 mmol NaCl). Positive standard sera containing anti-CCP2 referred to herein as RA, and negative standard sera using normal sera referred to herein as health control. One hundred microliters of the diluted sera were added to each well. After incubation for 1 hour at room temperature with shaking, the wells were washed three times with PBST. Horseradish peroxidase-conjugated goat anti-human IgG (Jackson ImmunoResearch Laboratories, West Grove, Pa.) diluted at 1:10000 in dilution buffer as reporter antibody was added at 100 µl per well and was incubated with shaking for 1 h at room temperature. After washing four times with PBST, the bound antibodies were detected with enzymatic substrate TMB. The reaction lasted for 30 min at room temperature under darkness and was stopped by addition of 100 µl of 2 M sulphuric acid per well. Plates were read at absorbance of wavelength 450 nm (A450). The antibody titer was expressed by means of an index calculated as ([A450 of measured sample serum–A450 of negative standard] divided by [A450 of positive standard–A450 of negative standard])×100. Intra-assay and inter-assay variations were <10%. The optimal cut-off value for the ELISA was determined from the receiver operating characteristic (ROC) curve.

Results

Sera samples were obtained from 55 patients diagnosed as RA according to the ACR criteria, and from 28 healthy subjects considered as control group and all the samples were screened by comprehensive medical testing. The results are presented in Table 2.

TABLE 2

Effect of Capture Antigen Composition on RA Test by ELISA

| Capture antigen | RA sera (%) (n = 55) | Control sera (%) (n = 28) |
|---|---|---|
| CCP2 | 67 | 0 |
| CitD1 | 89 | 0 |
| CitD2 | 98 | 0 |

Among the 55 RA patients, 37 were positive for anti-CCP2 antibody, 49 were positive for anti-CitD1, and 54 were positive for anti-CitD2. The diagnostic sensitivity expressed as percentage of true positives, was 67%, 89% and 98% for anti-CCP 2, anti-CitD1 and anti-CitD2, respectively. Of the sera that were reactive with CCP2, 81% were recognized by CitD1, and all of them were recognized by CitD2. Of the sera that were reactive with CitD1, 59% were recognized by CCP2, and all of them were recognized by CitD2. These results clearly evidence that amino acid residues other than Cit and Cys do not contribute to the sensitivity. The obtention of a sensitivity of 98% by using the linear dipeptide CitD2 as an antigenic substrate, demonstrates a marked and significant improvement compared with either the RF test or CCP2 test.

The contribution of Cys to the sensitivity was achieved by its participation in the epitope as a primary anchor residue rather than by participating outside the epitope as a neutral residue to constrain a peptide conformation that favor antibody binding.

Among the total of 28 control sera, none were positive for anti-CCP2, anti-CitD1 and anti-CitD2. Therefore, the diagnostic specificity, expressed as percentage of true negatives, was 100% for anti-CCP2, anti-CitD1 and anti-CitD2, respectively.

Applicant believes that neoepitopes, in particular those generated from native peptide ligations from incorporation of modified amino acids or peptides into NT-Cys residue via an amido bond, could also play a crucial role in other autoimmune diseases. Thus, the invention is also aimed toward epitopes at ligation site comprising Cys and modified amino acids or peptides that are reactive with autoantibodies from patients suffering from autoimmune diseases other than RA. Formation of neoepitopes by native peptide ligation are useful for the development of monoclonal antibodies against these diseases and for diagnosing the respective autoimmune diseases, in particular for the detection of autoantibodies in body fluid including blood, plasma and serum of patients who are suspected of suffering from the autoimmine diseases. Further, the epitopes and antibodies offer the possibility of developing organic compounds for new diagnoses and therapies including antigen-based immunointervention in the treatment of autoimmune diseases with the aid of combinational chemistry, which compounds are comprised within the scope of the invention.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated peptide selected from the group consisting of SEQ. ID. No. 1 and SEQ. ID. No. 2 wherein said peptide functions as an antigenic determinant for rheumatoid arthritis (RA).

2. A labeled peptide wherein the peptide is selected from the group consisting of SEQ. ID. No. 1 and SEQ. ID. No. 2.

3. A composition consisting essentially of the peptide of claim 1 in a carrier.

4. An enzyme-linked immunosorbent assay (ELISA) kit for conducting an RA test to determine presence of RA-specific autoantibody comprising the peptide of claim 1.

5. An isolated peptide in accordance with claim 1 wherein said peptide is SEQ. ID. No. 1.

6. An isolated peptide in accordance with claim 1 wherein said peptide is SEQ. ID. No. 2.

7. The peptide of claim 1, wherein the peptide of SEQ ID NO: 1 or SEQ ID NO: 2 is acetylated or alkylated.

8. The peptide of claim 5, wherein said peptide is acetylated or alkylated.

9. The peptide of claim 6, wherein said peptide is acetylated or alkylated.

10. The ELISA kit in accordance with claim 4 wherein said peptide is SEQ. ID. No. 1.

11. The ELISA kit in accordance with claim 4 wherein said peptide is SEQ. ID. No. 2.

12. The ELISA kit in accordance with claim 4 wherein the peptide of SEQ ID NO: 1 or SEQ ID NO: 2 is acetylated or alkylated.

13. The ELISA kit in accordance with claim 10 wherein said peptide is acetylated or alkylated.

14. The ELISA kit in accordance with claim 11, wherein said peptide is acetylated or alkylated.

* * * * *